(12) United States Patent
Libbus et al.

(10) Patent No.: US 8,918,190 B2
(45) Date of Patent: *Dec. 23, 2014

(54) IMPLANTABLE DEVICE FOR EVALUATING AUTONOMIC CARDIOVASCULAR DRIVE IN A PATIENT SUFFERING FROM CHRONIC CARDIAC DYSFUNCTION

(75) Inventors: Imad Libbus, St. Paul, MN (US); Badri Amurthur, Los Gatos, CA (US); Bruce H. KenKnight, Maple Grove, MN (US)

(73) Assignee: Cyberonics, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/314,133

(22) Filed: Dec. 7, 2011

(65) Prior Publication Data

US 2013/0158616 A1    Jun. 20, 2013

(51) Int. Cl.
*A61N 1/32* (2006.01)

(52) U.S. Cl.
USPC ............... 607/118; 607/17; 607/40; 607/116

(58) Field of Classification Search
USPC ..................... 607/17, 40, 116, 118
See application file for complete search history.

(56) References Cited

U.S. PATENT DOCUMENTS

| | | | |
|---|---|---|---|
| 5,522,854 A | 6/1996 | Ideker et al. | |
| 5,707,400 A * | 1/1998 | Terry et al. | 607/44 |
| 5,928,272 A | 7/1999 | Adkins et al. | |
| 5,978,709 A | 11/1999 | Begemann et al. | |
| 6,006,134 A | 12/1999 | Hill et al. | |
| 6,266,564 B1 | 7/2001 | Hill et al. | |
| 6,354,991 B1 | 3/2002 | Gross et al. | |
| 6,449,507 B1 | 9/2002 | Hill et al. | |
| 6,473,644 B1 | 10/2002 | Terry, Jr. et al. | |
| 6,508,771 B1 * | 1/2003 | Padmanabhan et al. | 600/515 |

(Continued)

FOREIGN PATENT DOCUMENTS

| | | |
|---|---|---|
| WO | WO9321824 | 11/1993 |
| WO | 03018113 | 3/2003 |

(Continued)

OTHER PUBLICATIONS

Li, Meihua, et al. "Vagal Nerve Stimulation Markedly Improves Long-Term Survival After Chronic Heart Failure in Rats." Dec. 8, 2003. American Heart Association. Circulation 2004:107:120-124. http://circ.ahajournals.org/content/109/1/120.*

(Continued)

*Primary Examiner* — Christopher D Koharski
*Assistant Examiner* — Michael Carey
(74) *Attorney, Agent, or Firm* — Cyberonics, Inc.

(57) ABSTRACT

An implantable device for evaluating autonomic cardiovascular drive in a patient suffering from chronic cardiac dysfunction is provided. A stimulation therapy lead includes helical electrodes configured to conform to an outer diameter of a cervical vagus nerve sheath, and a set of connector pins electrically connected to the helical electrodes. A neurostimulator includes an electrical receptacle into which the connector pins are securely and electrically coupled. The neurostimulator also includes a pulse generator configured to therapeutically stimulate the vagus nerve through the helical electrodes in alternating cycles of stimuli application and stimuli inhibition that are tuned to both efferently activate the heart's intrinsic nervous system and afferently activate the patient's central reflexes by triggering bi-directional action potentials. The neurostimulator includes a recordable memory storing a baseline heart rate. The neurostimulator includes an integrated leadless heart rate sensor configured to continually monitor heart rate in light of the baseline heart rate.

20 Claims, 4 Drawing Sheets

(56) References Cited

U.S. PATENT DOCUMENTS

| | | | |
|---|---|---|---|
| 6,522,926 B1 | 2/2003 | Kieval et al. |
| 6,600,954 B2 | 7/2003 | Cohen et al. |
| 6,610,713 B2 | 8/2003 | Tracey |
| 6,616,624 B1 | 9/2003 | Kieval |
| 6,622,041 B2 | 9/2003 | Terry, Jr. et al. |
| 6,652,449 B1 | 11/2003 | Gross et al. |
| 6,684,105 B2 | 1/2004 | Cohen et al. |
| 6,690,971 B2 | 2/2004 | Schauerte et al. |
| 6,712,772 B2 | 3/2004 | Cohen et al. |
| 6,718,208 B2 | 4/2004 | Hill et al. |
| 6,838,471 B2 | 1/2005 | Tracey |
| 6,839,594 B2 | 1/2005 | Cohen et al. |
| 6,850,801 B2 | 2/2005 | Kieval et al. |
| 6,862,480 B2 | 3/2005 | Cohen et al. |
| 6,892,098 B2 | 5/2005 | Ayal et al. |
| 6,896,651 B2 | 5/2005 | Gross et al. |
| 6,904,318 B2 | 6/2005 | Hill et al. |
| 6,907,295 B2 | 6/2005 | Gross et al. |
| 6,963,773 B2 | 11/2005 | Borschowa et al. |
| 6,963,779 B1 | 11/2005 | Shankar |
| 6,985,774 B2 | 1/2006 | Kieval et al. |
| 7,010,345 B2 | 3/2006 | Hill et al. |
| 7,072,720 B2 | 7/2006 | Puskas |
| 7,123,961 B1 | 10/2006 | Kroll et al. |
| 7,139,607 B1 | 11/2006 | Shelchuk |
| 7,158,832 B2 | 1/2007 | Kieval et al. |
| 7,184,828 B2 | 2/2007 | Hill et al. |
| 7,184,829 B2 | 2/2007 | Hill et al. |
| 7,218,964 B2 | 5/2007 | Hill et al. |
| 7,221,979 B2 | 5/2007 | Zhou et al. |
| 7,225,017 B1 | 5/2007 | Shelchuk |
| 7,225,019 B2 | 5/2007 | Jahns et al. |
| 7,237,320 B2 | 7/2007 | Lam |
| 7,245,967 B1 | 7/2007 | Shelchuk |
| 7,260,431 B2 | 8/2007 | Libbus et al. |
| 7,269,457 B2 | 9/2007 | Shafer et al. |
| 7,277,761 B2 | 10/2007 | Shelchuk |
| 7,295,881 B2 | 11/2007 | Cohen et al. |
| 7,305,265 B2 | 12/2007 | Fukui |
| 7,321,793 B2 | 1/2008 | Ben-Ezra et al. |
| 7,324,853 B2 | 1/2008 | Ayal et al. |
| 7,336,997 B2 | 2/2008 | Fukui |
| 7,346,398 B2 | 3/2008 | Gross et al. |
| 7,387,603 B2 | 6/2008 | Gross et al. |
| 7,389,149 B2 | 6/2008 | Rossing et al. |
| 7,395,119 B2 | 7/2008 | Hagen et al. |
| 7,403,819 B1 | 7/2008 | Shelchuk et al. |
| 7,418,292 B2 | 8/2008 | Shafer |
| 7,452,800 B2 | 11/2008 | Sosnowchik et al. |
| 7,480,532 B2 | 1/2009 | Kieval et al. |
| 7,481,759 B2 | 1/2009 | Whitehurst et al. |
| 7,485,104 B2 | 2/2009 | Kieval |
| 7,493,167 B2 | 2/2009 | Hussein et al. |
| 7,499,742 B2 | 3/2009 | Bolea et al. |
| 7,499,747 B2 | 3/2009 | Kieval et al. |
| 7,499,748 B2 | 3/2009 | Moffitt et al. |
| 7,502,650 B2 | 3/2009 | Kieval |
| 7,542,800 B2 | 6/2009 | Libbus et al. |
| 7,548,780 B2 | 6/2009 | Libbus et al. |
| 7,551,958 B2 | 6/2009 | Libbus et al. |
| 7,561,922 B2 | 7/2009 | Cohen et al. |
| 7,561,923 B2 | 7/2009 | Libbus et al. |
| 7,570,999 B2 | 8/2009 | Libbus et al. |
| 7,582,053 B2 | 9/2009 | Gross et al. |
| 7,584,004 B2 | 9/2009 | Caparso et al. |
| 7,587,238 B2 | 9/2009 | Moffitt et al. |
| 7,606,622 B2 | 10/2009 | Reeve |
| 7,613,511 B2 | 11/2009 | Wu et al. |
| 7,613,516 B2 | 11/2009 | Cohen et al. |
| 7,616,990 B2 | 11/2009 | Chavan et al. |
| 7,617,003 B2 | 11/2009 | Caparso et al. |
| 7,623,926 B2 | 11/2009 | Rossing et al. |
| 7,627,384 B2 | 12/2009 | Ayal et al. |
| 7,628,750 B2 | 12/2009 | Cohen et al. |
| 7,630,760 B2 | 12/2009 | Libbus et al. |
| 7,634,315 B2 | 12/2009 | Cholette |
| 7,634,317 B2 * | 12/2009 | Ben-David et al. ............. 607/14 |
| 7,640,057 B2 | 12/2009 | Libbus et al. |
| 7,647,101 B2 | 1/2010 | Libbus et al. |
| 7,650,190 B2 | 1/2010 | Zhou et al. |
| 7,657,312 B2 | 2/2010 | Pastore et al. |
| 7,660,628 B2 | 2/2010 | Libbus et al. |
| 7,664,548 B2 | 2/2010 | Amurthur et al. |
| 7,668,602 B2 | 2/2010 | Ben-David et al. |
| 7,672,633 B2 | 3/2010 | Kondoh |
| 7,676,275 B1 | 3/2010 | Farazi et al. |
| 7,689,286 B2 | 3/2010 | Pastore et al. |
| 7,711,415 B1 | 5/2010 | Farazi et al. |
| 7,711,421 B2 | 5/2010 | Shafer et al. |
| 7,734,355 B2 | 6/2010 | Cohen et al. |
| 7,751,884 B2 | 7/2010 | Ternes et al. |
| 7,769,442 B2 | 8/2010 | Shafer |
| 7,769,446 B2 | 8/2010 | Moffitt et al. |
| 7,778,702 B2 | 8/2010 | Ben-David et al. |
| 7,778,703 B2 | 8/2010 | Gross et al. |
| 7,778,711 B2 | 8/2010 | Ben-David et al. |
| 7,783,353 B2 | 8/2010 | Libbus et al. |
| 7,797,041 B2 | 9/2010 | Libbus et al. |
| 7,801,603 B2 | 9/2010 | Westlund et al. |
| 7,801,604 B2 * | 9/2010 | Brockway et al. ................ 607/3 |
| 7,801,614 B2 | 9/2010 | Rossing et al. |
| 7,805,193 B2 | 9/2010 | Libbus et al. |
| 7,805,203 B2 | 9/2010 | Ben-David |
| 7,813,805 B1 | 10/2010 | Farazi |
| 7,813,812 B2 | 10/2010 | Kieval et al. |
| 7,835,797 B2 | 11/2010 | Rossing et al. |
| 7,840,266 B2 | 11/2010 | Libbus et al. |
| 7,840,271 B2 | 11/2010 | Kieval et al. |
| 7,844,346 B2 | 11/2010 | Cohen et al. |
| 7,848,812 B2 | 12/2010 | Crowley et al. |
| 7,848,816 B1 | 12/2010 | Wenzel et al. |
| 7,869,869 B1 | 1/2011 | Farazi |
| 7,885,709 B2 | 2/2011 | Ben-David |
| 7,885,711 B2 | 2/2011 | Ben-Ezra |
| 7,890,185 B2 | 2/2011 | Cohen et al. |
| 7,894,907 B2 | 2/2011 | Cowan et al. |
| 7,904,151 B2 | 3/2011 | Ben-David |
| 7,904,175 B2 | 3/2011 | Scott et al. |
| 7,904,176 B2 | 3/2011 | Ben-Ezra et al. |
| 7,908,008 B2 | 3/2011 | Ben-David et al. |
| 7,916,013 B2 | 3/2011 | Stevenson |
| 7,925,342 B2 | 4/2011 | Amurthur et al. |
| 7,925,352 B2 | 4/2011 | Stack et al. |
| 7,974,693 B2 | 7/2011 | Ben-David et al. |
| 8,005,542 B2 | 8/2011 | Ben-Ezra et al. |
| 8,005,545 B2 | 8/2011 | Ben-David et al. |
| 8,036,745 B2 | 10/2011 | Ben-David et al. |
| 8,060,197 B2 | 11/2011 | Ben-David et al. |
| 8,065,021 B2 | 11/2011 | Gross et al. |
| 8,083,663 B2 | 12/2011 | Gross et al. |
| 8,116,881 B2 | 2/2012 | Cohen et al. |
| 8,131,362 B2 | 3/2012 | Moffitt et al. |
| 8,160,701 B2 | 4/2012 | Zhao et al. |
| 8,160,705 B2 | 4/2012 | Stevenson et al. |
| 8,195,290 B2 | 6/2012 | Brockway et al. |
| 8,224,436 B2 | 7/2012 | Libbus et al. |
| 8,249,711 B2 | 8/2012 | Libbus et al. |
| 8,369,943 B2 | 2/2013 | Shuros et al. |
| 8,386,038 B2 | 2/2013 | Bianchi et al. |
| 8,401,640 B2 | 3/2013 | Zhao et al. |
| 8,417,354 B2 | 4/2013 | Zhang et al. |
| 8,571,654 B2 | 10/2013 | Libbus et al. |
| 8,577,458 B1 | 11/2013 | Libbus et al. |
| 8,600,505 B2 | 12/2013 | Libbus et al. |
| 2002/0107553 A1 | 8/2002 | Hill et al. |
| 2003/0040774 A1 | 2/2003 | Terry et al. |
| 2005/0049655 A1 | 3/2005 | Boveja et al. |
| 2005/0065553 A1 | 3/2005 | Ben-Ezra et al. |
| 2005/0125044 A1 | 6/2005 | Tracey |
| 2005/0131467 A1 | 6/2005 | Boveja |
| 2005/0267542 A1 * | 12/2005 | David et al. ..................... 607/17 |
| 2006/0100668 A1 | 5/2006 | Ben-David et al. |
| 2006/0253161 A1 | 11/2006 | Libbus et al. |
| 2007/0067004 A1 | 3/2007 | Boveja et al. |

(56) References Cited

U.S. PATENT DOCUMENTS

| | | | |
|---|---|---|---|
| 2007/0093870 A1 | 4/2007 | Maschino et al. | |
| 2007/0179543 A1 | 8/2007 | Ben-David et al. | |
| 2007/0213773 A1 | 9/2007 | Hill et al. | |
| 2007/0233194 A1* | 10/2007 | Craig | 607/2 |
| 2007/0255320 A1 | 11/2007 | Inman et al. | |
| 2007/0276453 A1 | 11/2007 | Hill et al. | |
| 2008/0021503 A1 | 1/2008 | Whitehurst et al. | |
| 2008/0132983 A1 | 6/2008 | Cohen et al. | |
| 2008/0183258 A1 | 7/2008 | Inman | |
| 2008/0243196 A1 | 10/2008 | Libbus et al. | |
| 2009/0030493 A1 | 1/2009 | Colburn et al. | |
| 2009/0118777 A1 | 5/2009 | Iki et al. | |
| 2009/0124848 A1 | 5/2009 | Miazga | |
| 2009/0149900 A1 | 6/2009 | Moffitt et al. | |
| 2009/0248097 A1 | 10/2009 | Tracey et al. | |
| 2009/0270953 A1* | 10/2009 | Ecker et al. | 607/88 |
| 2010/0010556 A1* | 1/2010 | Zhao et al. | 607/17 |
| 2010/0010603 A1 | 1/2010 | Ben-David et al. | |
| 2010/0016919 A1 | 1/2010 | Hill et al. | |
| 2010/0042173 A1 | 2/2010 | Farazi et al. | |
| 2010/0114197 A1 | 5/2010 | Burnes et al. | |
| 2010/0286740 A1 | 11/2010 | Libbus et al. | |
| 2010/0331908 A1 | 12/2010 | Farazi | |
| 2011/0015692 A1 | 1/2011 | Libbus et al. | |
| 2011/0082514 A1 | 4/2011 | Libbus et al. | |
| 2011/0098796 A1 | 4/2011 | Ben-David et al. | |
| 2011/0224749 A1 | 9/2011 | Ben-David et al. | |
| 2011/0257708 A1 | 10/2011 | Kramer et al. | |
| 2011/0313488 A1 | 12/2011 | Hincapie Ordonez et al. | |
| 2012/0143286 A1 | 6/2012 | Hahn et al. | |
| 2012/0185007 A1 | 7/2012 | Ziegler et al. | |
| 2012/0185010 A1 | 7/2012 | Zhou et al. | |
| 2012/0303080 A1 | 11/2012 | Ben-David et al. | |
| 2013/0158617 A1 | 6/2013 | Libbus et al. | |
| 2013/0158618 A1 | 6/2013 | Libbus et al. | |
| 2013/0289646 A1 | 10/2013 | Libbus et al. | |

FOREIGN PATENT DOCUMENTS

| | | |
|---|---|---|
| WO | 03099373 | 12/2003 |
| WO | 03099377 | 12/2003 |
| WO | 03099377 A1 | 12/2003 |
| WO | 2004110549 | 12/2004 |
| WO | 2004110550 | 12/2004 |
| WO | 2005011805 | 2/2005 |
| WO | 2006019764 | 2/2006 |

OTHER PUBLICATIONS

Armour, J.A., "Potential clinical relevance of the 'little brain' on the mammalian heart," Experimental Physiology, vol. 93, No. 2, pp. 165-176 (Feb. 2008). Online Publication Date: Nov. 2, 2007. Available at: http://ep.physoc.org/content193/2/165.long.

Castoro et al., "Excitation properties of the right cervical vagus nerve in adult dogs," Experimental Neurology, vol. 227, iss. 1, pp. 62-68 (Jan. 2011). Online Publication Date: Sep. 17, 2010. Available at: http://www.sciencedirect.comiscience/article/pii/S001448861000347X.

De Ferrari et al., "Chronic vagus nerve stimulation: a new and promising therapeutic approach for chronic heart failure," European Heart Journal, vol. 32, iss. 7, pp. 847-855 (Apr. 2011). Online publication date: Oct. 28, 2010. Available at: http://eurheartj.oxfordjournals.org/content/32/7/847.long.

International Application No. PCT/US2013/021964, International Search Report and Written Opinion of the International Searching Authority dated Apr. 17, 2013, 10 pages.

International Application No. PCT/US2012/068205, International Search Report and Written Opinion of the International Searching Authority dated Feb. 8, 2013, 15 pages.

International Application No. PCT/US2012/068223, International Search Report and Written Opinion of the International Searching Authority dated Apr. 3, 2013, 11 pages.

International Application No. PCT/US2012/068213, International Search Report and Written Opinion of the International Searching Authority dated Mar. 15, 2013, 11 pages.

PCT Application No. PCT/US2013/021964, Search Report and Written Opinion dated Apr. 17, 2013, 10 pages.

PCT Application No. PCT/US2012/068205, Search Report and Written Opinion dated Feb. 8, 2013, 15 pages.

PCT Application No. PCT/US2012/068223, Search Report and Written Opinion dated Apr. 3, 2013, 11 pages.

PCT Application No. PCT/US2012/068213, Search Report and Written Opinion dated Mar. 15, 2013, 11 pages.

PCT Application No. PCT/US2012/068211, Search Report and Written Opinion dated May 7, 2013, 9 pages.

Armour, JA, "Potential clinical relevance of the 'little brain' on the mammalian heart," Experimental Physiology, vol. 1 93, No. 2, pp. 165-176 (Feb. 2008). Online Publication Date: Nov. 2, 2007. Available at: http://ep.physoc.org/ content/93/2/165.long.

Castoro et al.,"Excitation properties of the right cervical vagus nerve in adult dogs," Experimental Neurology, vol. 2 227, iss. 1, pp. 62-68 (Jan. 2011). Online Publication Date: Sep. 17, 2010. Available at: http://www.sciencedirecl.com/science/article/pii/SOO1448861000347X.

De Ferrari et al., "Chronic vagus nerve stimulation: a new and promising therapeutic approach for chronic heart failure," European Heart Journal, vol. 32, iss. 7, pp. 847-855 (Apr. 2011). Online publication date: Oct. 28, 2010. Available at: http://eurheartj.oxfordjournals.org/content/3217/84 7.long.

Klein et al., "Vagus nerve stimulation: A new approach to reduce heart failure," Cardiology Journal, vol. 17, iss. 6, pp. 638-643 (2010).

Li et al., "Vagal Nerve Stimulation Markedly Improves Long-Term Survival After Chronic Heart Failure in Rats," Circulation: Journal of the American Heart Association, vol. 109, iss. 1, pp. 120-124 (Jan. 2004). Online publication date: Dec. 8, 2003. Available at: http://circ.ahajournals.org/cgi/pmidlookup?view=long&pmid=14662714.

Olshansky et al., "Parasympathetic Nervous System and Heart Failure: Pathophysiology and Potential Implications for Therapy," Circulation: Journal of the American Heart Association, vol. 118, iss. 8, pp. 863-871 (Aug. 2008).

Sabbah et al., "Vagus nerve stimulation in experimental heart failure," Heart Failure Reviews, vol. 16, No. 2, pp. 171-178 (Mar. 2011). Online Publication Date: Dec. 3, 2010.

US 8,315,702, 11/2012, Chavan et al. (withdrawn).

Abraham, et al., "Devices in the management of advanced, chronic heart failure," Nature Reviews, vol. 10, pp. 98-110 (Feb. 2013) (Published online Dec. 11, 2012).

Adamson, et al., "Continuous Autonomic Assessment in Patients with Symptomatic Heart Failure: Prognostic Value of Heart Rate Variability Measured by an Implanted Cardiac Resynchronization Device," Circulation, Journal of the American Heart Association, 110, pp. 2389-2394 (2004).

Agostoni, et al., "Functional and Histological Studies of the Vagus Nerve and its Branches to the Heart, Lungs and Abdominal Viscera in the Cat," J. Physiol. 135, pp. 182-205 (1957).

Ajani, et al., "Prevalence of High C-Reactive Protein in Persons with Serum Lipid Concentrations within Recommended Values," Chemical Chemistry, 50:9, pp. 1618-1622 (2004).

Akiyama, et al., "Effects of right and left vagal stimulation on left ventricular acetylcholine levels in the cat," Acta Physiol Scand, 172, pp. 11-16 (2001).

Anand, et al., "C-Reactive Protein in Heart Failure: Prognostic Value and the Effect of Valsartan," Circulation, Journal of the American Heart Association, 112, pp. 1428-1434 (2005).

Anholt, et al., "Recruitment and blocking properties of the CardioFit stimulation lead," Journal of Neural Engineering, 8, pp. 1-6, (2011).

Ardell, et al., "Selective vagal innervation of sinoatrial and atrioventricular nodes in canine heart," Am. J. Physiol. 251 (Heart Circ. Physiol. 20), pp. H764-H773 (1986).

Armour, "Cardiac neuronal hierarchy in health and disease," Am J Physiol Regul Integr Comp Physiol, 287, pp. R262-R271 (2004).

Armour, "Myocardial ischaemia and the cardiac nervous system," Cardiovascular Research, 41, pp. 41-54 (1999).

Armour, "The little brain on the heart," Cleveland Clinic Journal of Medicine, vol. 74, supp. 1, pp. S48-S51 (Feb. 2007).

(56) References Cited

OTHER PUBLICATIONS

Armour, et al., "Functional anatomy of canine cardiac nerves," Acta anat., 91, pp. 510-528 (1975).
Armour, et al., "Localized myocardial responses to stimulation of small cardiac branches of the vagus," American Journal of Physiology, vol. 228, No. 1 pp. 141-148 (Jan. 1975).
Asala, et al., "An electron microscope study of vagus nerve composition in the ferret," Anat Embryol, 175, pp. 247-253 (1986).
Aukrust, et al., "Inflammatory and anti-inflammatory cytokines in chronic heart failure: Potential therapeutic implications," Annals of Medicine, 37, pp. 74-85 (2005).
Author Unknown, "Nerve fiber—Types and Function," www.boddunan.com Available at ww.boddunan.com/education/20-medicine-a-surgery/12730-nerver-fiber-types-and-function.html (Apr. 19, 2010).
Author Unknown, American Diabetes Association, "Standards of Medical Care in Diabetes—2012," Diabetes Care, vol. 35, supplement 1, pp. S11-S63 (Jan. 2012).
Author Unknown, Staff of Adinstruments, "Principles of Nerve Stimulation," Application Note, ADInstruments (Apr. 2002).
Bae, et al., "Gliosis in the Amygdala Following Myocardial Infarction in the Rat," J Vet Med Sci, 72(8), pp. 1041-1045 (2010).
Bernik, et al., "Pharmacological Stimulation of the Cholinergic Antiinflammatory Pathway," J. Exp. Med, vol. 195, No. 6, pp. 781-788 (Mar. 18, 2002).
Berthoud, et al., "Functional and chemical anatomy of the afferent vagal system," Autonomic Neuroscience: Basic and Clinical, 85, pp. 1-17 (2000).
Bhagat, et al., "Differential Effect of Right and Left Vagal Stimulation on Right and Left Circumflex Coronary Arteries," S A Medical Journal, 50, pp. 1591-1594 (1976).
Biasucci, et al., "Elevated Levels of C-Reactive Protein at Discharge in Patients with Unstable Angina Predict Recurrent Instability," Circulation,Journal of the American Heart Association, 99, pp. 855-860 (1999).
Bibevski, et al., "Evidence for impaired vagus nerve activity in heart failure," Heart Fail Rev, 16, pp. 129-135 (2011).
Bibevski, et al., "Ganglionic Mechanisms Contribute to Diminished Vagal Control in Heart Failure," Circulation, Journal of the American Heart Association, 99, pp. 2958-2963 (1999).
Bilgutay, et al., "Vagal Tuning a new concept in the treatment of supraventricular arrhythmias, angina pectoris, and heart failure," Journal of Thoracic and Cardiovascular Surgery, vol. 56, No. 1, pp. 71-82 (Jul. 1968).
Binkley, et al., "Parasympathetic Withdrawal is an Integral Component of Autonomic Imbalance in Congestive Heart Failure: Demonstration in Human Subjects and Verification in a Paced Canine Model of Ventricular Failure,"JACC, vol. 18, No. 2, pp. 464-472 (Aug. 1991).
Bois, et al., "Mode of action of bradycardic agent, S 16257, on ionic currents of rabbit sinoatrial node cells," Abstract, British Journal of Pharmacology, 118(4):1051-7 (1996).
Bonaz, et al., "Vagus nerve stimulation: From epilepsy to the cholinergic anti-inflammatory pathway," Neurogastroenterology & Motility, pp. 1-14 (2013).
Borggrefe, et al., "Vagal Stimulation Devices," ESC Congress 2010 (2010).
Borovikova, et al., "Vagus nerve stimulation attenuates the systemic inflammatory response to endotoxin," Nature, vol. 405, pp. 458-462 (May 25, 2000).
Brack, et al., "Mechanisms underlying the autonomic modulation of ventricular fibrillation initiation—tentative prophylactic properties in vagus nerve stimulation on malignant arrhythmias in heart failure," Heart Fail Rev (Published online Jun. 8, 2012).
Bronzino, "Biomedical Engineering Fundamentals," CRC Press, Chapter 30, pp. 30-10-30-15 (Apr. 2006).
Buschman, et al., "Heart Rate Control Via Vagus Nerve Stimulation," Neuromodulation, vol. 9, No. 3, pp. 214-220 (2006).
Butterwick, et al., "Tissue Damage by Pulsed Electrical Stimulation," IEEE Transactions on Biomedical Engineering, vol. 54, No. 12, pp. 2261-2267 (Dec. 2007).
Calkins, et al., "Comparison of Responses to Isoproterenol and Epinephrine During Head-Up Tilt in Suspected Vasodepressor Syncope," The American Journal of Cardiology, vol. 67 pp. 207-209 (Jan. 15, 1991).
Castoro, et al., "Excitation properties of the right cervical vagus nerve in adult dogs," Experimental Neurology, 227 (pp. 62-68 (2011).
Chapleau, et al., "Methods of assessing vagus nerve activity and reflexes," Heart Fail Rev, 16, pp. 109-127 (2011).
Chen, et al., "National and Regional Trends in Heart Failure Hospitalization and Mortality Rates for Medicare Beneficiaries, 1998-2008," JAMA, vol. 306, No. 15 (Oct. 19, 2011).
Chen, et al., "Role of Atrial Electrophysiology and Autonomic Nervous System in Patients with Supraventricular Tachycardia and Paroxysmal Artrial Fibrillation," J Am Coll Cardiol, vol. 32, No. 3, pp. 732-738 (Sep. 1998).
Cheng, et al., "Long-term Outcomes in Individuals with Prolonged PR Interval or First-Degree Atrioventricular Block," JAMA, vol. 301, No. 24 pp. 2571-2577 (Jun. 24, 2009).
Chiou, et al., "Effects of Continuous Enhanced Vagal Tone and Dual Atrioventricular Node and Accessory Pathways," Circulation, Journal of the American Heart Association, 107, pp. 2583-2588 (2003).
Cohen, et al., "Histopathology of the stimulated Vagus nerve: Primum non nocere," Heart Fail Rev, 16, pp. 163-169 (2011).
Colombo, et al., "Comparison between spectral analysis and the phenylephrine methods for the assessment of baroreflex sensitivity in chronic heart failure," Clinical Science, 97, pp. 503-513 (1999).
Cryan, et al., "Animal models and mood disorders: recent developments," Current Opinion in Psychiatry, 20, pp. 1-7 (2007).
Das, "Vagal nerve stimulation in prevention and management of coronary heart disease," World J. Cardiol, 3(4), pp. 105-110 (Apr. 26, 2011).
De Castro, et al., "Parasympathetic-mediated atrial fibrillation during tilt test associated with increased baroreflex sensitivity," The European Society of Cardiology, Europace, 8, pp. 349-351 (2006).
De Ferrari, et al., "Baroreflex Sensitivity Predicts Long-Term Cardiovascular Mortality After Myocardial Infarction Even in Patients with Preserved Left Ventricular Function," Journal of the American College of Cardiology, vol. 50, No. 24, pp. 2285-2290 (2007).
De Ferrari, et al., "Chronic Vagal Stimulation in Patients with Congestive Heart Failure," 31st Annual International Conference of the IEE EMBS (2009).
De Ferrari, et al., "Chronic vagus nerve stimulation: a new and promising therapeutic approach for chronic heart failure," European Heart Journal, 32, pp. 847-855 (2011).
De Ferrari, et al., "Vagus nerve stimulation: from pre-clinical to clinical application: challenges and future directions," Heart Fail Rev, 16, pp. 195-203 (2011).
De Jonge, et al., "Stimulation of the vagus nerve attenuates macrophage activation by activating the Jak2-STAT3 signaling pathway," Nature Immunology, vol. 6, No. 8, pp. 844-852 (Aug. 2005).
Desai, et al., "Pharmacologic modulation of parasympathetic activity in heart failure," Heart Fail Rev, 16, pp. 179-193 (Published online: Oct. 6, 2010) (2011).
Dickerson, et al., "Parasympathetic neurons in the cranial medial ventricular fat pad on the dog heart selectively decrease ventricular contractility," Journal of the Autonomic Nervous System, 70, pp. 129-141 (1998).
Dunlap, et al., "Mechanisms of altered vagal control in heart failure: influence of muscarinic receptors and acetylcholinesterase activity," Am J Physiol Heart Circ Physiol, 285, pp. H1632-H1640 (Jun. 26, 2003).
Elsenbruch, et al., "Heart Rate Variability During Waking and Sleep in Healthy Males and Females," SLEEP, vol. 22, No. 8, pp. 1067-1071 (1999).
Euler, et al., "Acetylcholine release by a stimulus train lowers atrial fibrillation threshold," Am. J Physiol. 253 (Heart Circ. Physiol, 22), pp. H863-H868 (1987).
Evans, et al., "Histological and functional studies on the fibre composition of the vagus nerve of the rabbit," Journal of Anatomy, 130, pp. 139-151 (1954).

(56) References Cited

OTHER PUBLICATIONS

Fallen, "Vagal Afferent Stimulation as a Cardioprotective Strategy? Introducing the Concept," A.N.E., vol. 10, No. 4 (Oct. 2005).
Fan, et al., "Transvenous vagus nerve stimulation: A potential heart failure therapy is feasible in humans," JACC, vol. 55, issue 10A, pp. E152-E153 (2010).
Fazan, et al., "Diabetic Peripheral Neuropathies: A Morphometric Overview," Int. J. Morphol, 28(I), pp. 51-64 (2010).
Feinauer, et al., "Ouabain enhances release of acetylcholine in the heart evoked by unilateral vagal stimulation," Arch Pharmacol, 333, pp. 7-12 (1986).
Fonarow, et al., "Incremental Reduction in Risk of Death Associated with Use of Gudeline-Recommended Therapies in Patients with Heart Failure: A Nested Case-Control Analysis of IMPROVE HF," J Am Heart Assoc, 1, pp. 16-26 (2012).
Ford, et al., "The effects of electrical stimulation of myelinated and non-myelinated vagal fibres on heart rate in the rabbit," J. Physiol. 380, pp. 341-347 (1986).
Furukawa, et al., "Effects of Verapamil, Zatebradine, and E-4031 on the Pacemaker Location and Rate in Response to Sympathetic Stimulation in Dog Hearts," The Journal of Pharmacology and Experimental Therapeutics, vol. 289, No. 3, pp. 1334-1342 (1999).
Furukawa, et al., "Selective inhibition by zatebradine and discrete parasympathetic stimulation of the positive chronotropic response to sympathetic stimulation in anesthetized dogs," Abstract, Journal of Pharmacology & Experimental Therapeutics, 272(2):744-9 (1995).
Gatti, et al., "Can neurons in the nucleus ambiguus selectively regulate cardiac rate and atrio-ventricular conduction?" Journal of the Autonomic Nervous System, 57, pp. 123-127 (1996).
Gatti, et al., "Vagal control of left ventricular contractility is selectively mediated by a cranioventricular intracardiac ganglion in the cat," Journal of the Autonomic Nervous System, 66, pp. 138-144 (1997).
Gibbons, et al., "Neuromodulation targets intrinsic cardiac neurons to attenuate neuronally mediated atrial arrhythmias," Am J Physiol Regul Integr Comp Physiol 302: R357-R364 (2012) (First published Nov. 16, 2011).
Gottdiener, et al., "Predictors of Congestive Heart Failure in the Elderly: The Cardiovascular Heatlh Study," Journal of the American College of Cardiology, vol. 35, No. 6, pp. 1628-1637 (2000).
Gray, et al., "Parasympathetic control of the Heart. II. A novel interganglionic intrinsic cardiac circuit mediates neural control of heart rate," J. Appl Physiol, 96, pp. 2273-2278 (2004).
Gray, et al., "Parasympathetic control of the Heart. III. Neuropeptide Y-immunoreactive nerve terminals synapse on three populations of negative chronotropic vagal preganglionic neurons," J. Appl Physiol, 96, pp. 2279-2287 (2004).
Grill, "Chapter 14—Principles of Electric Field Generation for Stimulation of the Central Nervous System," Neuromodulation, Academic Press (2009).
Guilleminault, et al., "Cyclical Variation of the Heart Rate in Sleep Apnoea Syndrome," The Lancet, pp. 126-131 (Jan. 21, 1984).
Hardwick, et al., "Chronic myocardial infarction induces phenotypic and functional remodeling in the guinea pig cardiac plexus," Am J Physiol Regulatory Integrative Comp Physiol, 295, pp. 1926-1933 (2008).
Hardwick, et al., "Remodeling of the guinea pig intrinsic cardiac plexus with chronic pressure overload," Am J Physiol Regulatory Integrative Comp Physiol, 297, pp. 859-866 (2009).
Hauptman, et al., "The vagus nerve and autonomic imbalance in heart failure: past, present, and future," Heart Fail Rev, 16, pp. 97-99 (2011).
Hirooka, et al., "Imbalance of central nitric oxide and reactive oxygen species in the regulation of sympathetic activity and neural mechanisms of hypertension," Am J Physiol Regulatory Integration Comp Physiol, 300, pp. 818-826 (2011).
Hoffman, et al., "Vagus Nerve Components," Anat Rec, 127, pp. 551-568 (1957).
Hu, et al., "Role of sympathetic nervous system in myocardial ischemia injury: Beneficial or deleterious?" Letters to the Editor, Elsevier Ireland Ltd. (Mar. 27, 2012).
Hua, et al., "Left vagal stimulation induces dynorphin release and suppresses substance P release from the rat thoracic spinal cord during cardiac ischemia," Am J Physiol Regulatory Integration Comp Physiol, 287, pp. 1468-1477 (2004).
Huston, et al., "Splenectomy inactivates the cholinergic antiinflammatory pathway during lethal endotoxemia and polymicrobial sepsis," J. Exp. Med, vol. 203, No. 7 pp. 1623-1628 (Jun. 19, 2006).
Huston, et al., "Transcutaneous vagus nerve stimulation reduces serum high mobility group box 1 levels and improves survival in murine sepsis," Crit Care Med, vol. 35, No. 12, pp. 2762-2768 (2007).
Ingemansson, et al., "Autonomic modulation of the atrial cycle length by the head up tilt test: non-invasive evaluation in patients with chronic atrial fibrillation," Heart, 80, pp. 71-76 (1998).
Ito, et al., "Efferent sympathetic and vagal innervation of the canine right ventricle," Circulation, Journal of the American Heart Association, vol. 90, pp. 1469-1468 (1994).
Jacques, et al., "Spinal Cord Stimulation Causes Potentiation of Right Vagus Nerve Effects on Atrial Chronotropic Function and Repolarization in Canines," Journal of Cardiovascular Electrophysiology, vol. 22, No. 4, pp. 440-447 (Apr. 2011).
Jaenisch, et al., "Respiratory muscle training improves baroreceptor sensitivity, decrease sympathetic tonus and increase vagal effect in rats with heart failure," European Heart Journal, 32 (Abstract Supplement, pp. 976 (2011).
Jammes, et al., "Afferent and efferent components of the bronchial vagal branches in cats," Journal of the Autonomic Nervous System, 5, pp. 165-176 (1982).
Janabi, et al., "Oxidized LDL-Induced NF-kB Activation and Subsequent Expression of Proinflammatory Genes are Defective in Monocyte-Derived Macrophages from CD36-Deficient Patients," Arterioscler Thromb Vasc Biol., 20:1953-1960 (2000).
Janse, et al., "Effects of unilateral stellate ganglion stimulation and ablation on electrophysiologic changes induced by acute myocardial ischemia in dogs," Circulation, Journal of the American Heart Association, 72, pp. 585-595 (1985).
Jessup, et al., "2009 Focused Update: ACCF/AHA Guidelines for the Diagnosis and Management of Heart Failure in Adults," Circulation, Journal of the American Heart Association, vol. 119, pp. 1977-2016 (2009).
Johnson, et al., "Parasympathetic control of the heart. I. An interventriculo-septal ganglion is the major source of the vagal intracardiac innervation of the ventricles," J Appl Physiol, 96, pp. 2265-2272 (2004).
Kakinuma, et al., "Cholinoceptive and cholinergic properties of cardiomyocytes involving an amplification mechanism for vagal efferent effects in sparsely innervated ventricular myocardium," FEBS Journal, 276, pp. 5111-5125 (2009).
Kalman, "Specific effects of zatebradine on sinus node function: suppression of automaticity, prolongation of sinoatrial conduction and pacemaker shift in the denervated canine heart," Abstract, Journal of Pharmacology & Experimental Therapeutics, 272(1):85-93 (1995).
Kaneko, et al., "C-Reactive Protein in Dilated Cardiomyopathy," Cardiology, 91, pp. 215-219 (1999).
Katare, et al., "Vagal nerve stimulation prevents reperfusion injury through inhibition of opening of mitochondrial permeability transition pore independent of bradycardiac effect," The Journal of Thoracic and Cardiovascular Surgery, vol. 137, No. 1, pp. 223-231 (2009).
Katz, et al., "Diseases of the heart in the Works of Hippocrates," Br Heart J, 24, pp. 257-264 (1962).
Kawada, et al., "High-frequency dominant depression of peripheral vagal control of heart rate in rats with chronic heart failure," Acta Physiol 207, 494-502 (2013).
Kawada, et al., "Vagal stimulation suppresses isschemia-induced myocardial interstitial norepinephrine release," Life Sciences, 78, pp. 882-887 (2006).
Kawashima, "The autonomic nervous system of the human heart with special reference to its origin, course, and peripheral distribution," Anat Embryol, 209, pp. 425-438 (2005).

(56) References Cited

OTHER PUBLICATIONS

Kliks, et al., "Influence of Sympathetic Tone on Ventricular Fibrillation Threshold During Experimental Coronary Occlusion," The American Journal of Cardiology, vol. 36, pp. 45-49 (Jul. 1975).
Kolman, et al., "The effect of vagus nerve stimulation upon vulnerability of the canine ventricle: role of sympathetic-parasympathetic interactions," Journal of the American Heart Association, 52, pp. 578-585 (1975).
Kong, et al., "Optimizing the Parameters of Vagus Nerve Stimulation by Uniform Design in Rats with Acute Myocardial Infarction," PLOS One, vol. 7, issue 11 (Nov. 2012).
Koopman, et al., "Pilot study of stimulation of the cholinergic anti-inflammatory pathway with an implantable vagus nerve stimulaton device in patients with rheumatoid arthritis," Abstract (2012).
Kulbertus, et al., ed., "Neurocardiology," Futura Publishing Co., pp. 13 ("Anatomy of the Cardiac Efferent Innvervation"); 61-63 ("Autonomic Neural Control"); 87, 89, 92-93 ("Sympathetic-Parasympathetic Interactions"); 183, 187 ("Parasympathetic Nervous System"); 104 (1988).
La Rovere, et al., "Baroreflex Sensitivity and Heart Rate Variability in the Identification of Patients at Risk for Life-Threatening Arrhythmias: Implications for Clinical Trials," Circulation, Journal of the American Heart Association, 103, pp. 2072-2077 (2001).
La Rovere, et al., "Baroreflex sensitivity and heart-rate variability in prediction of total cardiac mortality after myocardial infarction. ATRAMI (Autonomic Tone and Reflexes After Myocardial Infarction) Investigators," Lancet, 351(9101), pp. 478-484 (Feb. 14, 1998).
Lane, et al., "Prediction and Prevention of Sudden Cardiac Death in Heart Failure," Heart, 91, pp. 674-680 (2005).
Lechat, et al., "Heart rate and Cardiac Rhythm Relationships with Bisoprolol Benefit in Chronic Heart Failure in CIBIS II Trial," Circulation, Journal of American Heart Association, 103, pp. 1428-1433 (2001).
Lewis, et al., "Vagus nerve stimulation decreases left ventricular contractility in vivo in the human and pig heart," Journal of Physiology, 534, pp. 547-552 (2001).
Li, et al., "Early vagal stimulation markedly prevented cardiac dysfunction in rats after acute myocardial infarction in addition to suppressing arrhythmic death," European Heart Journal, 32 (Abstract Supplement), pp. 297-298 (2011).
Li, et al., "Inflammatory cytokines and nitric oxide in heart failure and potential modulation by vagus nerve stimulation," Heart Fail Rev, 16, pp. 137-145 (2011).
Li, et al., "Low-Level Vagosympathetic Stimulation. A Paradox and Potential New Modality for the Treatment of Focal Atrial Fibrillation," Circ Arrhythm Electrophysiol, Journal of American Heart Association, 2, pp. 645-651 (2009).
Li, et al., "Restoration of vagal tone by donepezil, on top of losartan treatment, markedly suppresses ventricular dysfunction and improves long-term survival in chronic heart failure rats," European Heart Journal, 32 (Abstract Supplement), pp. 642 (2011).
Li, et al., "Vagal nerve Stimulation Markedly Improves Long-Term Survival After Chronic Heart Failure in Rats," Circulation, Journal of the American Heart Association, 109, pp. 120-124 (2004).
Libby, et al., "Inflammation and Atherosclerosis," Circulation, Journal of the American Heart Association, 105, pp. 1135-1143 (2002).
Liu, et al., "Differing sympathetic and vagal effects on atrial fibrillation in dogs: role of refractoriness heterogeneity," Am. J. Physiol. 273 (Heart Circ. Physiol. 42), pp. H805-H816 (1997).
Lo, et al., "Paradoxical long-term proarrhythmic effects after ablating the 'head station' ganglionated plexi of the vagal innervation to the heart," Heart Rhythm, vol. 10, No. 5, pp. 751-757 (May 2013).
Lohmeier, et al., "Prolonged Activation of the Barorelfex Products Sustained Hypotension," Hypertension, Journal of the American Heart Association, 43, pp. 306-311 (2004).
Lu, et al., "Vagal nerve stimulation protects cardiac injury by attenuating mitochondrial dysfunction in a murine burn injury model," J. Cell. Mol. Med., vol. 17, No. 5, pp. 664-671 (2013).
Ma, et al., "Analysis of afferent, central, and efferent components of the baroreceptor reflex in mice," Am J Physiol Regulatory Integration Comp Physiol, 283, pp. 1033-1040 (2002).
Maj, et al., "P5775: Autonomic imbalance and circulating androgens and estrogens in men with systolic heart failure," European Heart Journal, 32 (Abstract Supplement), pp. 1090 (2011).
Malkin, et al., "Life-saving or life-prolonging? Interpreting trial data and survival curves for patients with congestive heart failure," The European Journal of Heart Failure, 7, pp. 143-148 (2005).
Mann, "Chapter 12—Peripheral Nerves," The Nervous System in Action, michaeldmann.net/mann12.html, (Jul. 2011).
Mann, "Inflammatory Mediators and the Failing Heart. Past, Present, and the Foreseeable Future," Circ Res., 91, pp. 988-998 (2002).
Mann, "Stress-Activated Cytokines and the Heart: From Adaptation to Maladaptation," Annu. Rev. Physiol., 65, pp. 81-101 (2003).
Martin-Portugues, et al., "Histopathologic features of the vagus nerve after electrical stimulation in swine," Histol Histopathol, 20, pp. 851-856 (2005).
Martins, et al., "Distribution of Local Repolarization Changes Produced by Efferent Vagal Stimulation in the Canine Ventricles," JACC, vol. 2, No. 6, pp. 1191-1199 (Dec. 1983).
Massari, et al., "Neural control of left ventricular contractility in the dog heart: synaptic interactions of negative inotropic vagal preganglionic neurons in the nucleus ambiguus and tyrosine hydroxylase immunoreactive terminals," Brain Research, 802, pp. 205-220 (1998).
May, et al., "P564: Long-term prediction of all-cause mortality in diabetic autonomic neuropathy: simple function tests or 24-hour heart rate variability (HRV)?" European Heart Journal, 32 (Abstract Supplement, pp. 64 (2011).
Mei,et al., "The Composition of the Vagus Nerve of the Cat," Cell Tissue Res., 209, pp. 423-431 (1980).
Merrill, et al., "Electrical stimulation of excitable tissue: design of efficacious and safe protocols," Journal of Neuroscience Methods, 141, pp. 171-198 (2005).
Mortara, et al., "Arterial Baroreflex Modulation of Heart Rate in Chronic Heart Failure," Circulation, Journal of the American Heart Association, vol. 96, No. 10, pp. 3450-3458 (Nov. 18, 1997).
Murakawa, et al., "Effect of Cervical Vagal Nerve Stimulation on Defibrillation Energy," Jpn Heart J, 44, pp. 91-100 (Jan. 2003).
Naito, "Effects of zatebradine and propranolol on canine ischemia and reperfusion-induced arrhythmias," European Journal of Pharmacology, 388, pp. 171-176 (2000).
Nakajima, et al., "Autonomic Control of the Location and Rate of the Cardiac Pacemaker in the Sinoatrial Fat Pad of Parasympathetically Denervated Dog Hearts," Journal of Cardiovascular Electrophysiology, vol. 13, No. 9 pp. 896-901 (Sep. 2002).
Nearing, et al., "Crescendo in Depolarization and Repolarization Heterogeneity Heralds Development of Ventricular Tachycardia in Hospitalized Patients with Decompensated Heart Failure," Circulation Arrhythmia and Electrophysiology, Journal of the American Heart Association, 5, pp. 84-90 (2012).
Nihei, et al., "Decreased Vagal Control Over Heart Rate in Rats with Right-Sided Congestive Heart Failure—Downregulation of Neuronal Nitric Oxide Synthase," Circ J, 69, pp. 493-499 (2005).
Ninomiya, "Direct Evidence of Nonuniform Distribution of Vagal Effects on Dog Atria," Circulation Research, vol. XIX, pp. 576-583 (Sep. 1966).
Nolan, et al., "Prospective Study of Heart Rate Variability and Mortality in Chronic Heart Failure: Results of the United Kingdom Heart Failure Evaluation and Assessment of Risk Trial (UK-Heart)," Circulation, Journal of the American Heart Association, 98, pp. 1510-1516 (1998).
Ochoa, et al., "P2497: Effects of insulin resistance on resting heart rate, baroreflex sensitivity and indices of autonomic cardiovascular modulation in individuals with high blood pressure levels," European Heart Journal, 32 (Abstract Supplement, pp. 431-432 (2011).
Ogawa, et al., "Left Stellate Ganglion and Vagal Nerve Activity and Cardiac Arrhythmias in Ambulatory Dogs with Pacing-Induced Congestive Heart Failure," Journal of the American College of Cardiology, vol. 50, No. 4, pp. 335-444 (2007).

(56) References Cited

OTHER PUBLICATIONS

Okada, et al., "Cyclic Stretch Upregulates Production of Interleukin-8 and Monocyte Chemotactic and Activating Factor/Monocyte Chemoattractant Protein-1 in Human Endothelial Cells," Arterioscler Thromb Vasc Biol., 18, pp. 894-901 (1998).

Oliveira, et al., "Effects of vagal stimulation on induction and termination of atrial fibrillation in an in vivo rabbit heart model," Rev Port Cardiol, 29(03), pp. 375-389 (2010).

Olshansky, et al., "Parasympathetic Nervous System and Heart Failure: Pathophysiology and Potential Implications for Therapy," Circulation, Journal of the American Heart Association, 118, pp. 863-871 (2008).

Onkka, et al., "Sympathetic nerve fibers and ganglia in canine cervical vagus nerves: Localization and quantitation," Heart Rhythm, vol. 10, No. 4, pp. 585-591 (Apr. 2013).

Ordelman, et al., "Selectivity for Specific Cardiovascular Effects of Vagal Nerve Stimulation with a Multi-Contact Electrode Cuff," IEEE, pp. 1-6 (2011).

Packer, et al., "Effect of Carvedilol on Survival in Severe Chronic Heart Failure," The New England Journal of Medicine, vol. 344, No. 22, pp. 1651-1658 (May 31, 2001).

Pavlov, et al., "Central muscarinic cholinergic regulation of the systemic inflammatory response during endotoxemia," PNAS, vol. 103, No. 13, pp. 5219-5223 (Mar. 28, 2006).

Pavlov, et al., "Controlling inflammation: the cholinergic anti-inflammatory pathway," Biochemical Society Transactions, vol. 34, part 6, pp. 1037-1040 (2006).

Peckham, et al., "Chapter 18—Implantable Neural Stimulators," Neuromodulation, Academic Press (2009).

Pina, et al., "The Predictive Value of Biomarkers in Heart Failure," Medscape Education Cardiology, Available at http://www.medscape.org/viewarticle/765328 (CME Released: Jun. 15, 2012).

Pitzalis, et al., "Comparison Between Noninvasive Indices of Baroreceptor Sensitivity and the Phenylephrine Method in Post-Myocardial Infarction Patients," Circulation, Journal of the American Heart Association, 97, pp. 1362-1367 (1998).

Poole-Wilson, "Relation of Pathophysiologic Mechanisms to Outcome in Heart Failure," JACC, vol. 22, No. 4 (supplement A), pp. 22A-29A (Oct. 1993).

Pye, et al., "Study of serum C-reactive protein concentration in cardiac failure," Br Heart J, 63, pp. 228-230 (1990).

Rademacher, et al., "P5878: Multidimensional holter-based analysis of cardiac autonomic regulation predicts early AF recurrence after electrical cardioversion," European Heart Journal, 32 (Abstract Supplement), pp. 1116-1117 (2011).

Randall, et al., "Regional vagosympathetic control of the heart," American Journal of Physiology, vol. 227, No. 2, pp. 444-452 (1974).

Randall, et al., "Selective Vagal Innervation of the Heart," Annals of Clinical and Laboratory Science, vol. 16, No. 3, pp. 198-208 (1986).

Raymond, et al., "Elevated interleukin-6 levels in patients with asymptomatic left ventricular systolic dysfunction," American Heart Journal, vol. 141, No. 3, pp. 435-438 (Mar. 2001).

Rhee, et al., "Presentation Abstract—Effects of suprathreshold vagal stimulation on stellate ganglion nerve activity in ambulatory dogs," 33rd Annual Scientific Sessions, Heart Rhythm (2012).

Riccio, et al., "Interganglionic segregation of distinct vagal afferent fibre phenotypes in guinea-pig airways," Journal of Physiology, 495. 2, pp. 521-530 (1996).

Riddle, et al., "Epidemiologic Relationships Between A1C and All-Cause Mortality During a Median 3.4-Year Follow-up of Glycemic Treatment in the ACCORD Trial," Diabetes Care, vol. 33, No. 5, pp. 983-990 (May 2010).

Ridker, C-Reactive Protein: A Simple Test to Help Predict Risk of Heart Attack and Stroke, Journal of the American Heart Association, 108, pp. e81-e85 (2003).

Ridker, et al., "Comparison of C-Reactive Protein and Low-Density Lipoprotein Cholesterol Levels in the Prediction of First cardiovascular Events," New England Journal of Medicine, vol. 347, No. 20, pp. 1557-1566 (Nov. 14, 2002).

Ridker, et al., "C-Reactive Protein and Other Markers of Inflammation in the Prediction of Cardiovascular Disease in Women," The New England Journal of Medicine, vol. 342, No. 12, pp. 836-841 (Mar. 23, 2000).

Ridker, et al., "Inflammation, Pravastatin, and the Risk of Coronary Events After Myocardial Infarction in Patients With Average Cholesterol Levels," Circulation, Journal of the American Heart Association, 98, pp. 839-844 (1998).

Roger, et al., "Heart Disease and Stroke Statistics—2011 Update: A Report from the American Heart Association," Circulation, Journal of the American Heart Association. Available at http://circ.ahajournals.org/content/123/4/e18 (2010).

Romanovsky, et al., "The vagus nerve in the thermoregulatory response to systemic inflammation," Am. J. Physiol., 273, pp. R407-R413 (1997).

Rossi, et al., "Epicardial ganglionated plexus stimulation decreases postoperative inflammatory response in humans," Heart Rhythm, vol. 9, No. 6, pp. 943-950 (Jun. 2012).

Rouse, et al., "The haemodynamic actions of ZENCA ZD7288, a novel sino-atrial node function modulator, in the exercising beagle: a comparison with zategradine and propranolol," Abstract, British Journal of Pharmacology, 113(3):1071-7 (1994).

Rozman, et al., "Heart function influenced by selective mid-cervical left vagus nerve stimulation in a human case study," Hypertension Research, 32, pp. 1041-1043 (2009).

Rutecki, "Anatomical, Physiological and Theoretical Basis for the Antiepileptic Effect of Vagus Nerve Stimulation," Epilepsia, 31 (suppl. 2), pp. S1-S6 (1990).

Sabbah, et al., "3722: Vagus nerve stimulation improves left ventricular function in heart failure: results of a 6 month investigation with a cross-over design in dogs with experimental heart failure," European Heart Journal, 32 (Abstract Supplement), pp. 642 (2011).

Sabbah, et al., "Baroreflex Activation Therapy for the Treatment of Heart Failure," Presentation available at http://www.cvrx.com/wp/wp-content/uploads/2012/04/Dr.-Sabbah-Slides.pdf (2012).

Sabbah, et al., "Chronic Electrical Stimulation of the Carotid Sinus Baroreflex Improves Left Ventricular Function and Promotes Reversal of Ventricular Remodeling in Dogs with Advanced Heart Failure," Circulation Heart Failure, Journal of the American Heart Association, 4, pp. 65-70 (2011).

Sabbah, et al., "Vagus nerve stimulation in experimental heart failure," Heart Fail Rev, 16, pp. 171-178 (2011).

Samara, et al., "The Effects of Cardiac Resyhchronization Therapy on Chronotropic Incompetence in Patients Intolerant of Beta Antagonist Therapy," Journal of Cardiac Failure, vol. 17, No. 8S, pp. S-54-S55 (Aug. 2011).

Sanner, et al., "P4743: Prediction of cardiovascular risk from nocturnal pulse wave signal using the autonomic state indicator (ASI) technology," European Heart Journal, 32 (Abstract Supplement), pp. 839 (2011).

Sato, et al., "Serial Circulating Concentrations of C-Reactive Protein, Interleukin (IL)-4, and IL-6 in Patients with Acute Left Heart Decompensation," Clin. Cardiol. 22, pp. 811-813 (1999).

Schauerte, "Time for Change: Cardiac neurophysiology meets cardiac electrophysiology," Editorial Commentary, Heart Rhythm Society (2013).

Schiereck, et al., "AV blocking due to asynchronous vagal stimulation in rats," Am J Physiol Heart Circ Physiol, 278, pp. H67-H73 (2000).

Schocken, et al., "Prevalence and Mortality Rate of Congestive Heart Failure in the United States," JACC, vol. 20, No. 2, pp. 301-306 (Aug. 1992).

Schwartz, "Vagal Stimulation for Heart Diseases: From Animals to Men," Circulation Journal, vol. 75, pp. 20-27 (Jan. 2011).

Schwartz, "Vagal stimulation for heart failure," Current Opinion in Cardiology, 26, pp. 51-54 (2011).

Schwartz, "Vagal stimulation for the treatment of heart failure: a translational success story," Heart, vol. 98, No. 23, pp. 1687-1690 (2012).

Schwartz, et al. Vagal stimulation for heart failure: Background and first in-man study, Heart Rhythm, 6, 11 suppl., pp. S76-S81 (Nov. 2009).

(56) References Cited

OTHER PUBLICATIONS

Schwartz, et al., "Autonomic mechanisms and sudden death. New insights from analysis of baroreceptor reflexes in conscious dogs with and without myocardial infarction," Circulation, Journal of the American Heart Association, 78, pp. 969-979 (1988).
Schwartz, et al., "Effects of Unilateral Cardiac Sympathetic Denervation on the Ventricular Fibrillation Threshold," The American Journal of Cardiology, vol. 37, pp. 1034-1040 (Jun. 1976).
Schwartz, et al., "Long term vagal stimulation in patients with advanced heart failure. First experience in man," European Journal of Heart Failure, 10, pp. 884-891 (2008).
Schwartz, et al., "Sympathetic-parasympathetic interaction in health and disease: abnormalities and relevance in heart failure," Heart Fail Rev, 16, pp. 101-107 (2011).
Seta, et al., "Basic Mechanisms in Heart Failure: The Cytokine Hypotehsis," Journal of Cardiac Failure, vol. 2, No. 3, pp. 243-249 (1996).
Sha, et al., "Low-Level Right Vagal Stimulation: Anticholinergic and Antiadrenergic Effects," J Cardiovasc Electrophysiol, pp. 1-7 (Feb. 2011).
Shamoon, et al., The Diabetes Control and Complications Trial Research Group, "The effect of intensive treatment of diabetes on the development and progression of long-term complications in insulin-dependent diabetes mellitus," The New England Journal of Medicine, vol. 329, No. 14, pp. 977-986 (Sep. 30, 1993).
Shannon, "A Model of Safe Levels for Electrical Stimulation," IEEE Transactions on Biomedical Engineering, vol. 39, No. 4, pp. 424-426 (Apr. 1992).
Shen, et al., "Continuous Low-Level Vagus Nerve Stimulation Reduces Stellate Ganglion Nerve Activity and Paroxysmal Atrial Tachyarrhythmias in Ambulatory Canines," Circulation, Journal of the American Heart Association, 123, pp. 2204-2212 (2011).
Shen, etl al., "Low-level vagus nerve stimulation upregulates small conductance calcium-activated potassium channels in the stellate ganglion," Heart Rhythm, vol. 10, No. 6, pp. 910-915 (2013).
Shinohara, et al., "Heart Failure Decreases Nerve Activity in the Right Atrial Ganglionated Plexus," J Cardiovasc Electrophysiol, pp. 1-9 (2011).
Shioi, et al., "Increased Expression of Interleukin-1B and Monocyte Chemotactic and Activating Factor/Monocyte Chemoattractant Protein-1 in the Hypertrophied and Failing Heart with Pressure Overload," Circ Res., 81, pp. 664-671 (1997).
Singal, et al., "The role of oxidative stress in the genesis of heart disease," Cardiovascular Research, 40, pp. 426-432 (1998).
Spuck, et al., "Right-sided vagus nerve stimulation in humans: An effective therapy?" Epilepsy Research, pp. 1-3 (2008).
Stein, et al., "A Simple Method to Identify Sleep Apnea Using Holter Recordings," J Cardiovasc Electrophysiol, vol. 14, pp. 467-473 (May 2003).
Stein, et al., "Feasibility of Using Mobile Cardiac Outpatient Telemetry (MCOT) to Identify Severe Sleep Disorders" (2009).
Stieber, et al., "Bradycardic and proarrhythmic properties of sinus node inhibitors," Abstract, Molecular Pharmacology, 69(4):1328-37 (2006).
Taylor, et al., "The unequal influences of the left and right vagi on the control of the heart and pulmonary artery in the rattlesnake, *Crotalus durissus*," The Journal of Experimental Biology, 212, pp. 145-151 (2009).
Thayer, et al., "The role of vagal function in the risk for cardiovascular disease and mortality," Biological Psychology, 74, pp. 224-242 (2007).
Thollon, et al., "Electrophysiological effects of S 16257, a novel sino-atrial node modulator, on rabbit and guinea-pig cardiac preparations: comparison with UL-FS 49," Abstract, British Journal of Pharmacology, 112(1):37-42 (1994).
Tosato, et al., "Quasi-trapezoidal pulses to selectively block the activation of intrinsic laryngeal muscles during vagal nerve stimulation," J. Neural Eng., 4, pp. 205-212 (2007).

Tsutsumi, et al., "Modulation of the myocardial redox state by vagal nerve stimulation after experimental myocardial infarction," Cardiovascular Research, 77, pp. 713-721 (2008).
Tyler, et al., "Chapter 17—Electrodes for the Neural Interface," Neuromodulation, Academic Press (2009).
Ulphani, et al., "Quantitative analysis of parasympathetic innervation of the porcine heart," Heart Rhythm, 7, pp. 1113-1119 (2010).
Uthman, et al., "Effectiveness of vagus nerve stimulation in epilepsy patients. A 12-year observation," Neurology, 63, pp. 1124-1126 (2004).
Van Stee, "Autonomic Innervation of the Heart," Environmental Health Perspectives, vol. 26, pp. 151-158 (1978).
Vanoli, et al., "Vagal stimulation and prevention of sudden death in conscious dogs with a healed myocardial infarction," Circulation Research, Journal of the American Heart Association, 68, pp. 1471-1481 (1991).
Vasan,. et al., "Inflammatory Markers and Risk of Heart Failure in Elderly Subjects Without Prior Myocardial Infarction," Circulation, Journal of the American Heart Association, 107, pp. 1486-1491 (2003).
Vassalle, et al., "An Analysis of Arrhythmias Induced by Ouabain in Intact Dogs," Circulation Research, Journal of the American Heart Association, 13, pp. 132-148 (1963).
Velagaleti, et al., "Long-Term Trends in the Incidence of heart Failure After Myocardial Infarction," 118, pp. 2057-2062 (2008).
Verrier, et al., "Microvolt T-Wave Alternans," Journal of the American College of Cardiology, vol. 58, No. 13, pp. 1309-1324 (2011).
Vimercati, et al., "Acute vagal stimulation attenuates cardiac metabolic response to B-adrenergic stress," The Journal of Physiology,vol. 500, No. 23, pp. 6065-6074 (2012).
Wang, et al., "Nicotinic acetylcholine receptor 7 subunit is an essential regulator of inflammation," Nature, vol. 421, pp. 384-388 (Jan. 23, 2003).
Wang, et al., "Synaptic and Neurotransmitter Activation of Cardiac Vagal Neurons in the Nucleus Ambiguus," Annals New York Academy of Sciences, pp. 237-246 (2001).
Waninger, et al., "Characterization of Atrioventricular Nodal Response to Electrical Left Vagal Stimulation," Annals of Biomedical Engineering, vol. 27, pp. 758-762 (1999).
Wann, "Behavioural signs of depression and apoptosis in the limbic system following myocardial infarction: effects of sertraline," Journal of Psychopharmacology, 23(4), pp. 451-459 (2009).
Wann, et al., "Vulnerability for apoptosis in the limbic system after myocardial infarction in rats: a possible model for human postinfarct major depression," J Psychiatry Neurosci, 32(1):11-6, pp. 11-16 (2007).
Watkins, et al., "Cytokine-to-Brain Communication: A Review & Analysis of Alternative Mechanisms," Life Sciences, vol. 57, No. 11, pp. 1011-1026 (1995).
Whyte, et al., "Reactive oxygen species modulate neuronal excitability in rat intrinsic cardiac ganglia," Auton Neurosci, 150(1-2), pp. 45-52 (Oct. 5, 2009).
Wieland, et al., "Bradycardic and proarrhythmic properties of sinus node inhibitors," Abstract, Molecular Pharmacology, 69(4):1328-37 (2006).
Yang, et al., "Sustained increases in heart rate induced by time repetition of vagal stimulation in dogs," Am. J. Physiol., 249, pp. H703-H709 (1985).
Yin, et al., "Independent prognostic value of elevated high-sensitivity C-reactive protein in chronic heart failure," American Heart Journal, vol. 147, No. 5, pp. 931-938 (2004).
Yndestad, et al., "Systemic inflammation in heart failure—The whys and wherefores," Heart Fail Rev, 11, pp. 83-92 (2006).
Yoo, et al., "High-resolution measurement of electrically-evoked vagus nerve activity in the anesthetized dog," J. Neural Eng., 10, pp. 1-9 (2013).
Yoo, et al., "Selective Control of Physiological Responses by Temporally-Patterned Electrical Stimulation of the Canine Vagus Nerve," 33rd Annual International Conference of the IEEE EMBS (2011).
Yu, et al., "Interactions between atrial electrical remodeling and autonomic remodeling: How to break the vicious cycle," Heart Rhythm, 9, pp. 804-809 (2012).

(56) References Cited

OTHER PUBLICATIONS

Yu, et al., "Low-level transcutaneous electrical stimulation of the auricular branch of the vagus nerve: A noninvasive approach to treat the initial phase of atrial fibrillation," Heart Rhythm, 10, pp. 428-435 (2013).

Yuan, et al., "Gross and Microscopic Anatomy of the Canine Intrinsic Cardiac Nervous System," The Anatomical Record, 239, pp. 75-87 (1994).

Yusuf, et al., "Changes in Hypertension Treatment and in Congestive Heart Failure Mortality in the United States," Hypertension, Journal of the American Heart Association, 13:I74-I179 (1989).

Zhang, et al., "Arrhythimias and vagus nerve stimulation," Heart Fail Rev, 16, pp. 147-161 (2011).

Zhang, et al., "Chronic Vagus Nerve Stimulation Improves Autonomic Control and Attenuates Systemic Inflammation and Heart Failure Progression in a Canine High-Rate Pacing Model," Journal of the American Heart Association, Circ Heart Fail, 2, pp. 692-699 (2009).

Zhang, et al., "Involvement of activated astrocyte and microglia of locus coeruleus in cardiac pain processing after acute cardiac injury," Neurol Res, 31, pp. 432-438 (2009).

Zhang, et al., "Relationship between right cervical vagus nerve stimulation and atrial fibrillation inducibility: Therapeutic intensities do not increase arrhythmogenesis," Heart Rhythm, 6, pp. 244-250 (2009).

Zhang, et al., "Therapeutic Effects of Selective Atrioventricular Node Vagal Stimulation in Atrial Fibrillation and Heart Failure," Journal of Cardiovascular Electrophysiology, vol. 24, Issue 1, pp. 86-91 (2012).

Zheng, et al., "Vagal stimulation markedly suppresses arrhythmias in conscioius rats with chronic heart failure after myocardial infarction," Proceedings of the 2005 IEEE (2005).

Zipes, et al., "Effects of selective vagal and stellate ganglion stimulation on atrial refractoriness," Cardiovascular Research, 8, pp. 647-655 (1974).

Zucker, et al., "Chronic Baroreceptor Activation Enhances Survival in Dogs with Pacing-Induced Heart Failure," Journal of the American Heart Association, Hypertension (2007).

PCT Application No. PCT/US2013/050390, Search Report and Written Opinion dated Nov. 5, 2013.

PCT Application No. PCT/US2013/068541, Search Report and Written Opinion dated Jan. 7, 2014.

* cited by examiner

IMPLANTABLE DEVICE FOR EVALUATING AUTONOMIC CARDIOVASCULAR DRIVE IN A PATIENT SUFFERING FROM CHRONIC CARDIAC DYSFUNCTION

FIELD

This application relates in general to chronic cardiac dysfunction therapy and, in particular, to an implantable device for evaluating autonomic cardiovascular drive in a patient suffering from chronic cardiac dysfunction.

BACKGROUND

Congestive heart failure (CHF) is a progressive and physically debilitating chronic medical condition in which the heart is unable to supply sufficient blood flow to meet the body's needs. CHF is a form of chronic cardiac dysfunction that affects nearly five million people each year in the United States alone and continues to be the leading cause of hospitalization for persons over the age of 65. CHF requires seeking timely medical attention.

Pathologically, CHF is characterized by an elevated neuroexitatory state that is accompanied by impaired arterial and cardiopulmonary baroreflex function and reduced vagal activity. CHF is initiated by cardiac dysfunction, which triggers compensatory activations of the sympathoadrenal (sympathetic) nervous and the renin-angiotensin-aldosterone hormonal systems. Initially, these two mechanisms help the heart to compensate for deteriorating pumping function. Over time, however, overdriven sympathetic activation and increased heart rate promote progressive left ventricular dysfunction and remodeling, and ultimately foretell poor long term patient outcome.

Anatomically, the heart is innervated by sympathetic and parasympathetic nerves originating through the vagus nerve and arising from the body's cervical and upper thoracic regions. The sympathetic and parasympathetic nervous systems, though separate aspects of the autonomous nervous system, dynamically interact thorough signals partially modulated by cAMP and cGMP secondary messengers. When in balance, each nervous system can presynaptically inhibit the activation of the other nervous system's nerve traffic. During CHF, however, the body suffers an autonomic imbalance of these two nervous systems, which leads to cardiac arrhythmogenesis, progressively worsening cardiac function, and eventual mortality.

Currently, the standard of care for managing chronic cardiac dysfunction, such as CHF, includes prescribing medication and mandating changes to a patient's diet and lifestyle, to counteract cardiac dysfunction. These medications include diuretics, angiotensin-converting enzyme inhibitors, angiotensin receptor blockers, beta-blockers, and aldosterone antagonists, which cause vasodilation, reduce secretion of vasopressin, reduce production and secretion of aldosterone, lower arteriolar resistance, increase venous capacity, increase cardiac output, index and volume, lower renovascular resistance, and lead to increased natriuresis, among other effects. The effectiveness of these medications is palliative, but not curative. Moreover, patients often suffer side effects and comorbidities, such as pulmonary edema, sleep apnea, and myocardial ischemia. Re-titration of drug therapy following crisis may be required, and neither continued drug efficacy nor patient survival are assured.

More recently, cardiac resynchronization therapy (CRT) has become available to patients presenting with impairment of systolic function, such as is caused by an intraventricular conduction delay or bundle-branch block that forces the heart's ventricles to contract dyssynchronously. Typically, implantable CRT devices use a set of biventricular leads to stimulate both the ventricular septum and the lateral wall of the left ventricle. CRT restores the synchronous beating of the heart through coordinated pacing of both ventricles. However, CRT is only helpful for treating systolic dysfunction and is not indicated for patients presenting with preserved ejection fraction. Thus, CRT is limited to patients exhibiting a wide QRS complex and mechanical dyssynchrony, whereas patients presenting with systolic dysfunction or impaired ejection fraction and a narrow QRS have limited therapeutic options.

Medication and CRT are only partial solutions to managing chronic cardiac dysfunction, and neural stimulation has been proposed as an alternative way to treat chronic cardiac dysfunction conditions, such as CHF, by correcting the underlying autonomic imbalance of the sympathetic and parasympathetic nervous systems. The heart contains an intrinsic nervous system that includes spatially-distributed sensory afferent neurons, interconnecting local circuit neurons, and motor adrenergic and cholinergic efferent neurons. Peripheral cell stations of these neurons activate under the tonic influence of spinal cord and medullary reflexes and circulating catecholamines to influence overlapping regions of the heart. Suppression of excessive neural activation by electrically modulating select vagal nerve fibers may help improve the heart's mechanical function as well as to reduce the heart's intrinsic nervous system's propensity to induce atrial arrhythmias during autonomic imbalance.

Electrical vagus nerve stimulation (VNS) is currently used clinically for the treatment of drug-refractory epilepsy and depression, and is under investigation for applications in Alzheimer's disease, anxiety, heart failure, inflammatory disease, and obesity. In particular, vagus nerve stimulation has been proposed as a long-term therapy for the treatment of CHF, as described in Sabbah et al., "Vagus Nerve Stimulation in Experimental Heart Failure," Heart Fail. Rev., 16:171-178 (2011), the disclosure of which is incorporated by reference. The Sabbah paper discusses canine studies using a vagus stimulation device, manufactured by BioControl Medical Ltd., Yehud, Israel, which includes a signal generator, right ventricular sensing lead, and right vagus nerve cuff stimulation lead. The sensing leads enable stimulation of the right vagus nerve to be synchronized to the cardiac cycle through feedback on-demand heart rate control. A bipolar nerve cuff electrode was surgically implanted on the right vagus nerve at the mid-cervical position. Electrical stimulation to the right cervical vagus nerve was delivered only when heart rate increased beyond a preset level to reduce basal heart rate by ten percent. Self-titration using "magnet mode" was impracticable in light of the test subject, here canine. Stimulation was provided at an impulse rate and intensity intended to keep the heart rate within a desired range by preferential stimulation of efferent nerve fibers leading to the heart while blocking afferent neural impulses to the brain. An asymmetric bi-polar multi-contact cuff electrode was employed to provide cathodic induction of action potentials while simultaneously applying asymmetric anodal blocks that were expected to lead to preferential, but not exclusive, activation of vagal efferent fibers. Although effective in restoring baroreflex sensitivity and, in the canine model, significantly increasing left ventricular ejection fraction and decreasing left ventricular end diastolic and end systolic volumes, restoration of autonomic balance was left unaddressed.

Other uses of electrical nerve stimulation for therapeutic treatment of various physiological conditions are described.

For instance, U.S. Pat. No. 6,600,954, issued Jul. 29, 2003 to Cohen et al. discloses a method and apparatus for selective control of nerve fibers. At least one electrode device is applied to a nerve bundle capable, upon activation, of generating unidirectional action potentials to be propagated through both small diameter and large diameter sensory fibers in the nerve bundle, and away from the central nervous system. The device is particularly useful for reducing pain sensations, such as propagating through the legs and arms.

U.S. Pat. No. 6,684,105, issued Jan. 27, 2004 to Cohen et al. discloses an apparatus for treatment of disorders by unidirectional nerve stimulation. An apparatus for treating a specific condition includes a set of one or more electrode devices that are applied to selected sites of the central or peripheral nervous system of the patient. For some applications, a signal is applied to a nerve, such as the vagus nerve, to stimulate efferent fibers and treat motility disorders, or to a portion of the vagus nerve innervating the stomach to produce a sensation of satiety or hunger. For other applications, a signal is applied to the vagus nerve to modulate electrical activity in the brain and rouse a comatose patient, or to treat epilepsy and involuntary movement disorders.

U.S. Pat. No. 7,123,961, issued Oct. 17, 2006 to Kroll et al. discloses stimulation of autonomic nerves. An autonomic nerve is stimulated to affect cardiac function using a stimulation device in electrical communication with the heart by way of three leads suitable for delivering multi-chamber stimulation and shock therapy. In addition, the device includes a fourth lead having three electrodes positioned in or near the heart, or near an autonomic nerve remote from the heart. Power is delivered to the electrodes at a set power level. The power is delivered at a reduced level if cardiac function was affected.

U.S. Pat. No. 7,225,017, issued May 29, 2007 to Shelchuk discloses terminating ventricular tachycardia. Cardioversion stimulation is delivered upon detecting a ventricular tachycardia. A stimulation pulse is delivered to a lead having one or more electrodes positioned proximate to a parasympathetic pathway. Optionally, the stimulation pulse is delivered post inspiration or during a refractory period to cause a release of acetylcholine.

U.S. Pat. No. 7,277,761, issued Oct. 2, 2007 to Shelchuk discloses vagal stimulation for improving cardiac function in heart failure or CHF patients. An autonomic nerve is stimulated to affect cardiac function using a stimulation device in electrical communication with the heart by way of three leads suitable for delivering multi-chamber stimulation and shock therapy. In addition, the device includes a fourth lead having three electrodes positioned in or near the heart, or near an autonomic nerve remote from the heart. A need for increased cardiac output is detected and a stimulation pulse is delivered through an electrode, for example, proximate to the left vagosympathetic trunk or branch to thereby stimulate a parasympathetic nerve. If the stimulation has caused sufficient increase in cardiac output, ventricular pacing may then be initiated at an appropriate reduced rate.

U.S. Pat. No. 7,295,881, issued Nov. 13, 2007 to Cohen et al. discloses nerve branch-specific action potential activation, inhibition and monitoring. Two preferably unidirectional electrode configurations flank a nerve junction from which a preselected nerve branch issues, proximally and distally to the junction, with respect to the brain. Selective nerve branch stimulation can be used in conjunction with nerve-branch specific stimulation to achieve selective stimulation of a specific range of fiber diameters, substantially restricted to a preselected nerve branch, including heart rate control, where activating only the vagal B nerve fibers in the heart, and not vagal A nerve fibers that innervate other muscles, can be desirous.

U.S. Pat. No. 7,778,703, issued Aug. 17, 2010 to Gross et al. discloses selective nerve fiber stimulation for treating heart conditions. An electrode device is adapted to be coupled to a vagus nerve of a subject and a control unit drives the electrode device by applying to the vagus nerve a stimulating current and also an inhibiting current, which are capable of respectively inducing action potentials in a therapeutic direction in a first set and a second set of nerve fibers in the vagus nerve and inhibiting action potentials in the therapeutic direction in the second set of nerve fibers only. The nerve fibers in the second set have larger diameters than the nerve fibers in the first set. The control unit typically drives the electrode device to apply signals to the vagus nerve to induce the propagation of efferent action potentials towards the heart and suppress artificially-induced afferent action potentials toward the brain.

U.S. Pat. No. 7,813,805, issued Oct. 12, 2010 to Farazi and U.S. Pat. No. 7,869,869, issued Jan. 11, 2011 to Farazi both disclose subcardiac threshold vagal nerve stimulation. A vagal nerve stimulator is configured to generate electrical pulses below a cardiac threshold of the heart, which are transmitted to a vagal nerve, so as to inhibit or reduce injury resulting from ischemia. The cardiac threshold is a threshold for energy delivered to the heart above which there is a slowing of the heart rate or conduction velocity. In operation, the vagal nerve stimulator generates the electrical pulses below the cardiac threshold, such that heart rate is not affected.

Finally, U.S. Pat. No. 7,885,709, issued Feb. 8, 2011 to Ben-David discloses nerve stimulation for treating disorders. A control unit can be configured to drive an electrode device to stimulate the vagus nerve, so as to modify heart rate variability, or to reduce heart rate, by suppressing the adrenergic (sympathetic) system. The vagal stimulation reduces the release of catecholamines in the heart, thereby lowering adrenergic tone at its source. For some applications, the control unit synchronizes the stimulation with the subject's cardiac cycle, while for other applications, the stimulation can be applied, for example, in a series of pulses. To reduce heart rate, stimulation is applied using a target heart rate lower than the subject's normal average heart rate.

Accordingly, a need remains for an approach to therapeutically treating chronic cardiac dysfunction, including CHF, through a form of electrical stimulation of the cervical vagus nerve to confirm pre-therapeutic cardiovascular drive and subsequently restore autonomic balance.

SUMMARY

Excessive sustained activation of the sympathetic nervous system has a deleterious effect on long term cardiac performance and ultimately on the survival of chronic cardiac dysfunction patients. Bi-directional afferent and efferent neural stimulation through the vagus nerve can beneficially restore autonomic balance and improve long term patient outcome. Stimulus delivery can be provided through a vagal neurostimulator per a schedule specified in stored stimulation parameters or based on sensory-based therapy triggers provided through an integrated heart rate sensor.

One embodiment provides a vagus nerve neurostimulator for evaluating autonomic cardiovascular drive. An implantable neurostimulator includes a pulse generator configured to drive electrical therapeutic stimulation tuned to restore autonomic balance through electrical pulses continuously and periodically delivered in both afferent and efferent directions of the cervical vagus nerve through a pair of helical electrodes via an electrically coupled nerve stimulation therapy lead. The implantable neurostimulator also includes a leadless heart rate sensor configured to continually monitor heart rate against a stored baseline heart rate.

A further embodiment provides an implantable device for evaluating autonomic cardiovascular drive. An implantable neurostimulator device includes a pulse generator configured to deliver both afferent and efferent therapeutic electrical stimulation to a cervical vagus nerve in continuous alternating cycles of stimuli application and stimuli inhibition. A cervical vagus nerve stimulation therapy lead is electrically coupled to the pulse generator and is terminated by a pair of helical electrodes through which the therapeutic electrical stimulation is delivered to the cervical vagus nerve. An integrated leadless heart rate sensor configured to continually monitor heart rate against a baseline heart rate stored in a memory in the pulse generator.

A still further embodiment provides an implantable device for evaluating autonomic cardiovascular drive in a patient suffering from chronic cardiac dysfunction. A cervical vagus nerve stimulation therapy lead includes a pair of helical electrodes configured to conform to an outer diameter of a cervical vagus nerve sheath of a patient and a set of connector pins electrically connected to the helical electrodes by an insulated electrical lead body. A neurostimulator is powered by a primary battery and enclosed in a hermetically sealed housing. The neurostimulator includes an electrical receptacle included on an outer surface of the housing into which the connector pins are securely and electrically coupled. The neurostimulator also includes a pulse generator configured to therapeutically stimulate the cervical vagus nerve through the helical electrodes in alternating cycles of stimuli application and stimuli inhibition that are tuned to both efferently activate the heart's intrinsic nervous system and afferently activate the patient's central reflexes by triggering bi-directional action potentials. The neurostimulator further includes a recordable memory within which is stored a baseline heart rate for the patient prior to stimulation therapy initiation. Finally, the neurostimulator includes an integrated leadless heart rate sensor configured to continually monitor the patient's heart rate in light of the baseline heart rate.

By restoring autonomic balance, therapeutic VNS operates acutely to decrease heart rate, increase heart rate variability and coronary flow, reduce cardiac workload through vasodilation, and improve left ventricular relaxation. Over the long term, VNS provides the chronic benefits of decreased negative cytokine production, increased baroreflex sensitivity, increased respiratory gas exchange efficiency, favorable gene expression, renin-angiotensin-aldosterone system down-regulation, and anti-arrhythmic, anti-apoptotic, and ectopy-reducing anti-inflammatory effects.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

The sympathetic nervous system affects cardiovascular physiology in an "all-or-nothing" form of neurological response, whereas the parasympathetic nervous system selectively modulates specific regions of the heart at various levels of activation. Through these two nervous systems, the autonomic nervous system directly controls the heart by affecting conduction, refractoriness, impulse formation, and the electrophysiological properties of the cardiac tissue, and indirectly by influencing the heart's homodynamics, blood flow, and metabolism, as well as exercising control over other body functions that rely on the heart.

The sympathetic and parasympathetic nervous systems dynamically interact thorough signals partially modulated by cAMP and cGMP secondary messengers to presynaptically influence the activation of each other's nerve traffic. Changes to one nervous system can indirectly affect nerve activation in the other. For instance, during autonomic imbalance, sympathetic neural activity increases while cardiac vagal activation, and therefore sympathetic innervation, is withdrawn. In view of their collaborative influence over cardiac function, the restoration of autonomic balance between these nervous systems is crucial to managing chronic cardiac dysfunction.

Conventional therapeutic alteration of cardiac vagal efferent activation through electrical stimulation of sympathetic vagal nerve fibers can produce beneficial bradycardia and modification in atrial and ventricular contractile function. However, such targeting of only the efferent nerves of the sympathetic nervous system is clinically insufficient to restore autonomic balance, as any affect on parasympathetic activation merely occurs due to incidental recruitment of parasympathetic nerve fibers. In contrast, propagating bi-directional action potentials through parasympathetic afferent and efferent nerve fibers in the vagus nerve resulting from neural stimulation engages both medullary and cardiac reflex control components and works to directly restore autonomic balance by engaging both components of both nervous systems. Moreover, many of the conventional approaches to VNS monitor heart rate through an intracardiac lead, typically implanted into the right ventricle and adapted from sensing leads used in pacemakers and defibrillators. Implantation of these leads is surgically complex and increases risk of injury to the patient and post-surgical complications.

Figure 1:
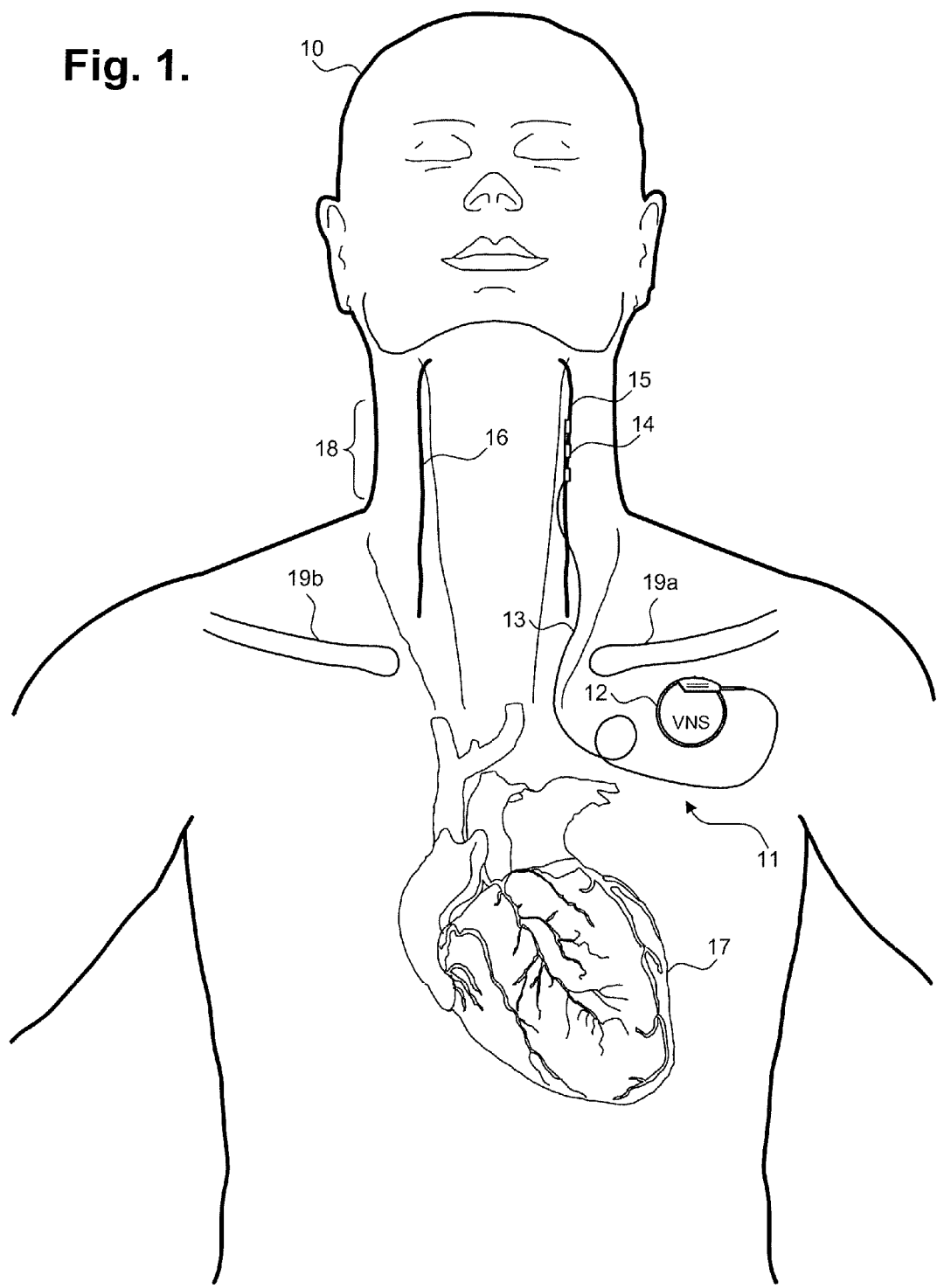
FIG. 1 is a front anatomical diagram showing, by way of example, placement of an implantable vagus stimulation device in a male patient, in accordance with one embodiment.

An implantable vagus nerve stimulator with integrated heart rate sensor, such as used to treat drug-refractory epilepsy and depression, can be adapted to use in managing chronic cardiac dysfunction through therapeutic bi-directional vagal stimulation. In addition, an integrated heart rate sensor can allow the patient's heart rate to be determined prior to the initiation of therapy delivery, or the heart rate can be provided to the stimulator from an external source. FIG. 1 is a front anatomical diagram showing, by way of example, placement of an implantable vagus stimulation device 11 in a male patient 10, in accordance with one embodiment. The VNS provided through the stimulation device 11 operates under several mechanisms of action. These mechanisms include increasing parasympathetic outflow and inhibiting sympathetic effects by blocking norepinephrine release. More importantly, VNS triggers the release of acetylcholine (ACh) into the synaptic cleft, which has beneficial anti-arrhythmic, anti-apoptotic, and ectopy-reducing anti-inflammatory effects.

The implantable vagus stimulation device 11 includes three main components, an implantable neurostimulator 12, a therapy lead 13, and helical electrodes 14. In addition, the operation of the neurostimulator 12 can be remotely checked, downloaded, diagnosed, and programmed by healthcare professionals using an external programmer (as further described below with reference to FIG. 3). Together, the implantable vagus stimulation device 11 and the external programmer form a VNS therapeutic delivery system.

The neurostimulator 12 is implanted in the patient's right or left pectoral region generally on the same side of the patient's body as the vagus nerve 15, 16 to be stimulated. A subcutaneous pocket is formed in the subclavicular region into which the neurostimulator 12 is placed. The helical electrodes 14 are generally implanted on the vagus nerve 15, 16 about halfway between the clavicle 19a-b and the mastoid process. The therapy lead 13 and helical electrodes 14 are implanted by first exposing the carotid sheath and chosen vagus nerve 15, 16 through a latero-cervical incision on the ipsilateral side of the patient's neck 18. The helical electrodes 14 are then placed onto the exposed nerve sheath and tethered. A subcutaneous tunnel is formed between the respective implantation sites of the neurostimulator 12 and helical electrodes 14, through which the therapy lead 13 is guided to the neurostimulator 12 and securely connected.

Anatomically, the vagus nerve includes a pair of nerve fiber bundles 15, 16 that both proceed laterally through the neck, thorax, and abdomen, and distally innervate the heart 17 and other major organs and body tissue. The stimulation device 11 bi-directionally stimulates the vagus nerve 15, 16 through application of continuous, periodic electrical stimuli. Both sympathetic and parasympathetic nerve fibers are stimulated through the helical electrodes 14 of the stimulation device 11. Stimulation of the cervical vagus nerve results in propagation of action potentials in both afferent and efferent directions from the site of stimulation. Afferent action potentials propagate toward the parasympathetic nervous system's origin in the medulla in the nucleus ambiguus, nucleus tractus solitarius, and the dorsal motor nucleus, as well as towards the sympathetic nervous system's origin in the intermediolateral cell column of the spinal cord.

Efferent action potentials propagate toward the heart to innervate the components of the heart's intrinsic nervous system. Intracardially, the cardiac nervous system is conceived as two major outflow branches exerting reciprocal control over cardiac indices under sole influence of central neuronal command. The outflow branches respectively regulate adrenergic (sympathetic) and cholinergic (parasympathetic) efferent preganglionic neuronal activity. Innervation of the heart 17 is regionalized and exhibits a high degree of asymmetry. Within the heart 17, the greatest concentration of vagal nerves is found first in the sinus node and then in the atrioventricular node. Cardiac efferents of the left vagus nerve 15 regulate cardiac contractility through their influence on conduction in the atrioventricular (AV) node. Cardiac efferents of the right vagus nerve 16 affect sinus node automaticity and regulate heart rate. Thus, right-sided cervical vagal stimulation tends to produce sinus bradycardia, whereas left-sided cervical vagal stimulation tends to produce AV nodal blockage.

Either the left or right vagus nerve 15, 16 can be stimulated by the stimulation device 11, although stimulation of the left vagus nerve 15 is preferred because stimulation of the left vagus nerve 15 is less likely to be arrhythmogenic. The left vagus nerve 15 has fewer projections to the sinoatrial node and is therefore less likely to severely reduce heart rate. Left VNS increases AV nodal conduction time and refractory period. In current form, VNS elicits bi-directional activation of both afferent and efferent nerve fibers. The balance between achieving therapeutic benefits (afferent) and side-effects (efferent) is largely determined by the threshold differences between activation of the different vagus nerve fibers.

Figure 2:
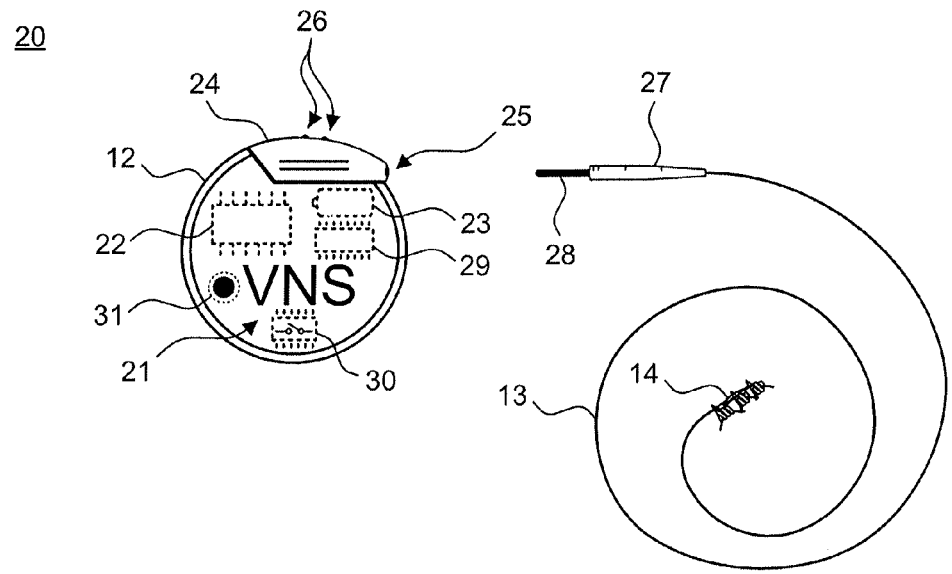
FIG. 2 is a diagram showing the implantable neurostimulator and simulation therapy lead of FIG. 1 with the therapy lead unplugged.

The VNS therapy is autonomously delivered to the patient's vagus nerve 15, 16 through three implanted components, a neurostimulator 12, therapy lead 13, and helical electrodes 14. FIG. 2 is a diagram showing the implantable neurostimulator 12 and simulation therapy lead 13 of FIG. 1 with the therapy lead unplugged 20. In one embodiment, the neurostimulator 12 can be adapted from a VNS Therapy AspireSR Model 106 generator, manufactured and sold by Cyberonics, Inc., Houston, Tex., although other manufactures and types of single-pin receptacle implantable VNS neurostimulators with integrated leadless heart rate sensors could also be used. The stimulation therapy lead 13 and helical electrodes 14 are generally fabricated as a combined assembly and can be adapted from a Model 302 lead, PerenniaDURA Model 303 lead, or PerenniaFLEX Model 304 lead, all of which are also manufactured and sold by Cyberonics, Inc., in two sizes based on helical electrode inner diameter, although other manufactures and types of single-pin receptacle-compatible therapy leads and electrodes could also be used.

The neurostimulator 12 provides continuous alternating ON-OFF cycles of vagal stimulation that when applied to the vagus nerve through the electrodes 14, produce action potentials in the underlying nerves that propagate bi-directionally; afferently propagating action potentials activate the medial medullary sites responsible for central reflex control and efferently propagating action potentials activate the heart's intrinsic nervous system. Cardiac motor neurons, when activated, influence heart rate, AV nodal conduction, and atrial and ventricular inotropy, thereby providing chronic cardiac dysfunction therapeutic effects. In addition, the alternating cycles can be tuned to activate phasic parasympathetic response in the vagus nerve 15, 16 being stimulated by bi-directionally modulating vagal tone.

The neurostimulator 12 includes an electrical pulse generator that drives electrical therapeutic stimulation, which is tuned to restore autonomic balance, through electrical pulses that are continuously and periodically delivered in both afferent and efferent directions of the vagus nerve 15, 16. The neurostimulator 12 is enclosed in a hermetically sealed housing 21 constructed of a biocompatible, implantation-safe material, such as titanium. The housing 21 contains electronic circuitry 22 powered by a primary battery 22, such as a lithium carbon monoflouride battery. The electronic circuitry 22 is implemented using complementary metal oxide semiconductor integrated circuits that include a microprocessor that executes a control program according to the stored stimulation parameters as programmed into the neurostimulator 12; a voltage regulator that regulates system power; logic and control circuitry, including a recordable memory 29 within which the stimulation parameters are stored, that controls overall pulse generator function, receives and implements programming commands from the external programmer, or other external source, and collects and stores telemetry information, processes sensory input, and controls scheduled and sensory-based therapy outputs; a transceiver that remotely communicates with the external programmer using radio frequency signals; an antenna, which receives programming instructions and transmits the telemetry information to the external programmer; and a reed switch 30 that provides a manually-actuatable mechanism to place the neurostimulator into an on-demand stimulation mode or to inhibit stimulation, also known as "magnet mode." Other electronic circuitry and components, such as an integrated heart rate sensor, are possible.

The neurostimulator 12 delivers VNS under control of the electronic circuitry 22, particularly the logic and control circuitry, which control stimulus delivery per a schedule specified in the stored stimulation parameters, based on sensory-based therapy triggers (as further described infra) or on-demand in response to magnet mode, a programming wand instruction, or other external source. The stored stimulation parameters are programmable (as further described below with reference to FIG. 7). In addition, sets of preselected stimulation parameters can be provided to physicians through the external programmer and fine-tuned to a patient's physiological requirements prior to being programmed into the neurostimulator 12, such as described in commonly-assigned U.S. Patent Publication No. 2013-0158618A1, entitled "Computer-Implemented System and Method for Selecting Therapy Profiles of Electrical Stimulation of Cervical Vagus Nerves for Treatment of Chronic Cardiac Dysfunction," Ser. No. 13/314,138, filed on Dec. 7, 2011, pending, the disclosure of which is incorporated by reference. The magnet mode can be used by the patient 10 to exercise on-demand manual control over the therapy delivery and titration of the neurostimulator, such as described in commonly-assigned U.S. Pat. No. 8,600,505, entitled "Implantable Device for Facilitating Control of Electrical Stimulation of Cervical Vagus Nerves for Treatment of Chronic Cardiac Dysfunction," Ser. No. 13/314,130, filed on Dec. 7, 2011, the disclosure of which is incorporated by reference. The stimulation parameters also include the levels of stimulation for the bi-directional action potentials.

Externally, the neurostimulator 12 includes a header 24 to securely receive and connect to the therapy lead 13. In one embodiment, the header 24 encloses a receptacle 25 into which a single pin for the therapy lead 13 can be received, although two or more receptacles could also be provided, along with the requisite additional electronic circuitry 22. The header 24 internally includes a lead connector block (not shown) and a set of set screws 26.

The therapy lead 13 delivers an electrical signal from the neurostimulator 12 to the vagus nerve 15, 16 via the helical electrodes 14. On a proximal end, the therapy lead 13 has a lead connector 27 that transitions an insulated electrical lead body to a metal connector pin 28. During implantation, the connector pin 28 is guided through the receptacle 25 into the header 24 and securely fastened in place using the set screws 26 to electrically couple the therapy lead 13 to the neurostimulator 12. On a distal end, the therapy lead 13 terminates with the helical electrode 14, which bifurcates into a pair of anodic and cathodic electrodes 62 (as further described below with reference to FIG. 4). In one embodiment, the lead connector 27 is manufactured using silicone and the connector pin 28 is made of stainless steel, although other suitable materials could be used, as well. The insulated lead body 13 utilizes a silicone-insulated alloy conductor material.

The housing 21 also contains a heart rate sensor 31 that is electrically interfaced with the logic and control circuitry, which receives the patient's sensed heart rate as sensory inputs. The heart rate sensor 31 monitors heart rate using an ECG-type electrode. Through the electrode, the patient's heart beat can be sensed by detecting ventricular depolarization. In a further embodiment, a plurality of electrodes can be used to sense voltage differentials between electrode pairs, which can be signal processed and combined into other cardiac physiological measures, for instance, P, QRS and T complexes. These cardiac artifacts can be used to derive other physiological measures and diagnose abnormal rhythm disorders and indicia, including sleep apnea, hypopnea index, dysautonomias (postural orthostatic tachycardia syndrome (POTS), vasovagal syncope, inappropriate sinus tachycardia (IST), and the like), and arrhythmia detection (atrial fibrillation, ventricular tachycardia, ventricular fibrillation, heart block, and so forth). Other direct and indirect uses of the heart rate sensor 31 are possible. In one embodiment, the heart rate sensor 31 can be adjusted for sensitivity and is capable of detecting heart beats in the range of 20 to 240 bpm. Other levels and ranges of heart beat sensitivity are possible.

Prior to the initiation of titration and eventual therapeutic stimulation, the neurostimulator 12 remains idle, yet the time period between implantation and therapy initiation provides an opportunity to passively monitor the patient's heart rate or other physiology, depending upon the capabilities of the neurostimulator 12. Ordinarily, the heart rate sensor 31 provides the sensed heart rate to the control and logic circuitry as sensory inputs, which can be stored as data in the recordable memory 29. When sensed prior to therapy initiation, the sensory inputs of the heart rate sensor 31 can be used as a baseline heart rate, which reflects the pre-therapeutic condition of the patient's cardiovascular drive. The sensed heart rate 29 can be chosen as either a direct measurement of heart rate, or statistically by taking an average, minimum, maximum, or mean heart rate over time. Other ways of determining a baseline heart rate through use of the heart rate sensor 29 or other sensory-input sources or devices integrated into the neurostimulator 12 are possible.

Once therapy has begun, the sensory inputs of the heart rate sensor 31 serve as sensory-based therapy triggers to autonomously titrate VNS delivery in light of the baseline heart rate. The logic and control circuitry can then determine whether the stimulation needs to be adjusted or inhibited. Alternatively, the baseline heart rate can be programmed into the neurostimulator 12 using, for instance, an external programmer. Importantly, the baseline heart rate need not necessarily be based on the patient's heart rate per se; non-heart rate ECG measurements, for example, could be used to derive the baseline heart rate and then programmed into the neurostimulator 12. Other ways of determining a baseline heart rate from a source outside of the neurostimulator 12 are possible.

Therapy can be adjusted whenever the sensed heart rate falls out of bounds relative to the baseline heart rate, such as outside of a predetermined heart rate range. A lower bound, stored in the recordable memory 29, can be set to indicate bradycardia or an asystolic heart condition. The lower bound can be expressed as a ratio, percentile, or function, of the baseline heart rate, or as discrete independent (absolute) values with respect to the baseline heart rate. If the heart rate sensed by the heart rate sensor 31 falls below the lower bound on the baseline heart rate, the neurostimulator 12 can be instructed, through the stimulation parameters, to suspend the triggering of the bi-directional action potentials altogether. Therapy can also be programmed to resume automatically after a fixed time period. Alternatively, the neurostimulator 12 can be instructed to down titrate therapy by gradually adjusting the stimulation parameters downwards until the bradycardia or asystole are no longer present. Therapy can also be programmed to gradually up titrate by adjusting the stimulation parameters upwards after first inhibiting stimulation for a fixed time period. Both the down titration and the up titration can occur stepwise, where the changes in the stimulation parameters occur in small increments spread out over time, rather than all at once. VNS therapy can be titrated by adjusting the stored stimulation parameters, including output current, pulse width, and signal frequency, to different VNS therapeutic setting that are less intense (down titrate) or more intense (up titrate). An upper bound, stored in the recordable memory 29, can also be set to indicate insufficient therapy delivery. The upper bound can be expressed as a ratio, percentile, or function, of the baseline heart rate, or as discrete independent (absolute) values with respect to the baseline heart rate. If the heart rate sensed by the heart rate sensor 31 rises above an upper bound on the baseline heart rate, the neurostimulator 12 can be instructed, again through the stimulation parameters, to up titrate the triggering of the bi-directional action potentials and thereby lower heart rate.

Figure 3:
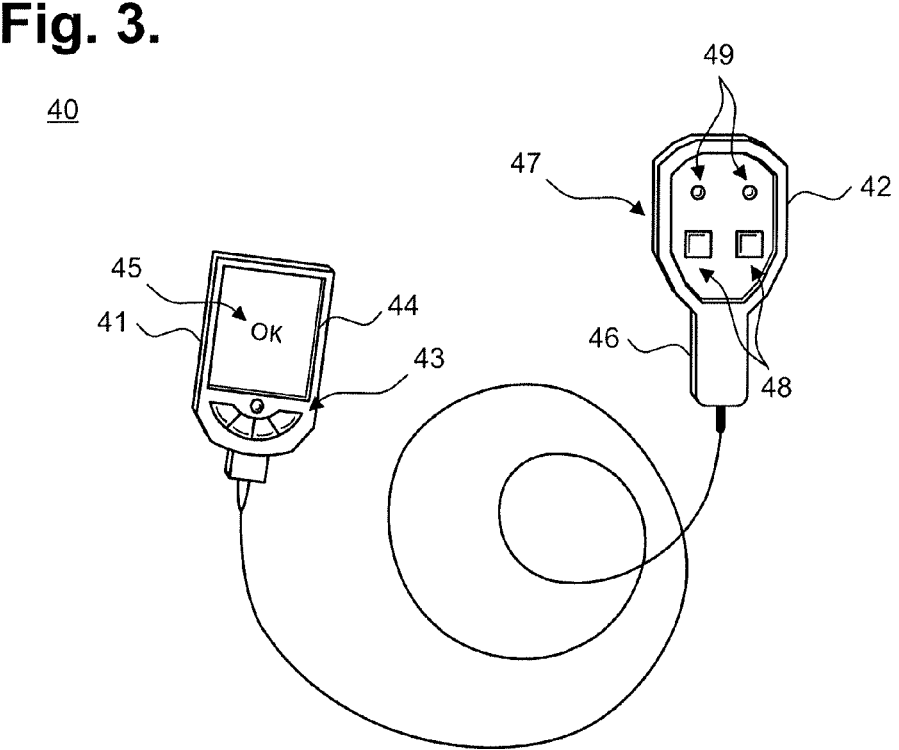
FIG. 3 is a diagram showing an external programmer for use with the implantable neurostimulator of FIG. 1.

The neurostimulator 12 is preferably interrogated prior to implantation and throughout the therapeutic period for checking proper operation, downloading recorded data, diagnosing problems, and programming operational parameters. FIG. 3 is a diagram showing an external programmer 40 for use with the implantable neurostimulator 12 of FIG. 1. The external programmer 40 includes a healthcare provider-operable programming computer 41 and a programming wand 42. Generally, use of the external programmer 40 is restricted to healthcare providers, while more limited manual control is provided to the patient through "magnet mode."

In one embodiment, the programming computer 41 executes application software specially designed to interrogate the neurostimulator 12. The programming computer 41 interfaces to the programming wand 42 through a standardized wired data connection, including a serial data interface, for instance, an EIA RS-232 or USB serial port. Alternatively, the programming computer 41 and the programming wand 42 could interface wirelessly. The programming wand 42 can be adapted from a Model 201 Programming Wand, manufactured and sold by Cyberonics, Inc. Similarly, the application software can be adapted from the Model 250 Programming Software suite, licensed by Cyberonics, Inc. Other configurations and combinations of computer 41, programming wand 42, and application software 45 are possible.

The programming computer 41 can be implemented using a general purpose programmable computer and can be a personal computer, laptop computer, netbook computer, handheld computer, or other form of computational device. In one embodiment, the programming computer is a personal digital assistant handheld computer operating under the Pocket-PC or Windows Mobile operating systems, licensed by Microsoft Corporation, Redmond, Wash., such as the Dell Axim X5 and X50 personal data assistants, sold by Dell, Inc., Round Top, Tex., the HP Jornada personal data assistant, sold by Hewlett-Packard Company, Palo Alto, Tex. The programming computer 41 functions through those components conventionally found in such devices, including, for instance, a central processing unit, volatile and persistent memory, touch-sensitive display, control buttons, peripheral input and output ports, and network interface. The computer 41 operates under the control of the application software 45, which is executed as program code as a series of process or method modules or steps by the programmed computer hardware. Other assemblages or configurations of computer hardware, firmware, and software are possible.

Operationally, the programming computer 41, when connected to a neurostimulator 12 through wireless telemetry using the programming wand 42, can be used by a healthcare provider to remotely interrogate the neurostimulator 12 and modify stored stimulation parameters. The programming wand 42 provides data conversion between the digital data accepted by and output from the programming computer and the radio frequency signal format that is required for communication with the neurostimulator 12.

The healthcare provider operates the programming computer 41 through a user interface that includes a set of input controls 43 and a visual display 44, which could be touch-sensitive, upon which to monitor progress, view downloaded telemetry and recorded physiology, and review and modify programmable stimulation parameters. The telemetry can include reports on device history that provide patient identifier, implant date, model number, serial number, magnet activations, total ON time, total operating time, manufacturing date, and device settings and stimulation statistics and on device diagnostics that include patient identifier, model identifier, serial number, firmware build number, implant date, communication status, output current status, measured current delivered, lead impedance, and battery status. Other kinds of telemetry or telemetry reports are possible.

During interrogation, the programming wand 42 is held by its handle 46 and the bottom surface 47 of the programming wand 42 is placed on the patient's chest over the location of the implanted neurostimulator 12. A set of indicator lights 49 can assist with proper positioning of the wand and a set of input controls 48 enable the programming wand 42 to be operated directly, rather than requiring the healthcare provider to awkwardly coordinate physical wand manipulation with control inputs via the programming computer 41. The sending of programming instructions and receipt of telemetry information occur wirelessly through radio frequency signal interfacing. Other programming computer and programming wand operations are possible.

Figure 4:
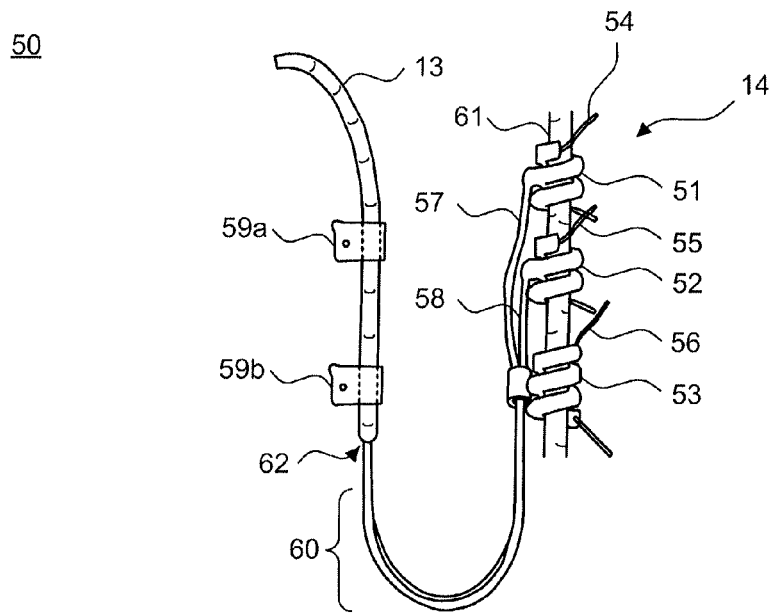
FIG. 4 is a diagram showing the helical electrodes provided as on the stimulation therapy lead of FIG. 2 in place on a vagus nerve in situ.

Preferably, the helical electrodes 14 are placed over the cervical vagus nerve 15, 16 at the location below where the superior and inferior cardiac branches separate from the cervical vagus nerve. FIG. 4 is a diagram showing the helical electrodes 14 provided as on the stimulation therapy lead 13 of FIG. 2 in place on a vagus nerve 15, 16 in situ 50. Although described with reference to a specific manner and orientation of implantation, the specific surgical approach and implantation site selection particulars may vary, depending upon physician discretion and patient physical structure.

The helical electrodes 14 are positioned over the patient's vagus nerve 61 oriented with the end of the helical electrodes 14 facing the patient's head. At the distal end, the insulated electrical lead body 13 is bifurcated into a pair of lead bodies 57, 58 that are connected to a pair of electrodes proper 51, 52. The polarity of the electrodes 51, 52 could be configured into a monopolar cathode, a proximal anode and a distal cathode, or a proximal cathode and a distal anode. In addition, an anchor tether 53 is fastened over the lead bodies 57, 58 that maintains the helical electrodes' position on the vagus nerve 61 following implant. In one embodiment, the conductors of the electrodes 51, 52 are manufactured using a platinum and iridium alloy, while the helical materials of the electrodes 51, 52 and the anchor tether 53 are a silicone elastomer.

During surgery, the electrodes 51, 52 and the anchor tether 53 are coiled around the vagus nerve 61 proximal to the patient's head, each with the assistance of a pair of sutures 54, 55, 56, made of polyester or other suitable material, which help the surgeon to spread apart the respective helices. The lead bodies 57, 58 of the electrodes 51, 52 are oriented distal to the patient's head and aligned parallel to each other and to the vagus nerve 61. A strain relief bend 60 can be formed on the distal end with the insulated electrical lead body 13 aligned parallel to the helical electrodes 14 and attached to the adjacent fascia by a plurality of tie-downs 59a-b.

In one embodiment, the stimulation protocol calls for a six-week titration period. During the first three-weeks, the surgical incisions are allowed to heal and no VNS therapy occurs. During the second three-weeks, the neurostimulator 12 is first turned on and operationally tested. The impulse rate and intensity of the VNS is then gradually increased every three or four days until full therapeutic levels of stimulation are achieved, or maximal patient tolerance is reached, whichever comes first. Patient tolerance can be gauged by physical discomfort or pain, as well as based on presence of known VNS side-effects, such as ataxia, coughing, hoarseness, or dyspnea.

Therapeutically, the VNS is delivered through continual alternating cycles of electrical pulses and rest (inhibition), which is specified to the neurostimulator 12 through the stored stimulation parameters. The neurostimulator 12 can operate either with or without an integrated heart rate sensor, such as respectively described in commonly-assigned U.S. Pat. No. 8,577,458, entitled "Implantable Device for Providing Electrical Stimulation of Cervical Vagus Nerves for Treatment of Chronic Cardiac Dysfunction with Leadless Heart Rate Monitoring," Ser. No. 13/314,126, filed on Dec. 7, 2011, and U.S. patent application, entitled "Implantable Device for Providing Electrical Stimulation of Cervical Vagus Nerves for Treatment of Chronic Cardiac Dysfunction," Ser. No. 13/314,119, filed on Dec. 7, 2011, pending, the disclosures of which are incorporated by reference. Additionally, where an integrated leadless heart rate sensor is available, the neurostimulator 12 can provide self-controlled titration, such as described in commonly-assigned U.S. Patent Publication No. 2013-0158617 A1, entitled "Implantable Device for Providing Electrical Stimulation of Cervical Vagus Nerves for Treatment of Chronic Cardiac Dysfunction with Bounded Titration," Ser. No. 13/314,135, filed on Dec. 7, 2011, pending, the disclosure of which is incorporated by reference.

Figure 5:
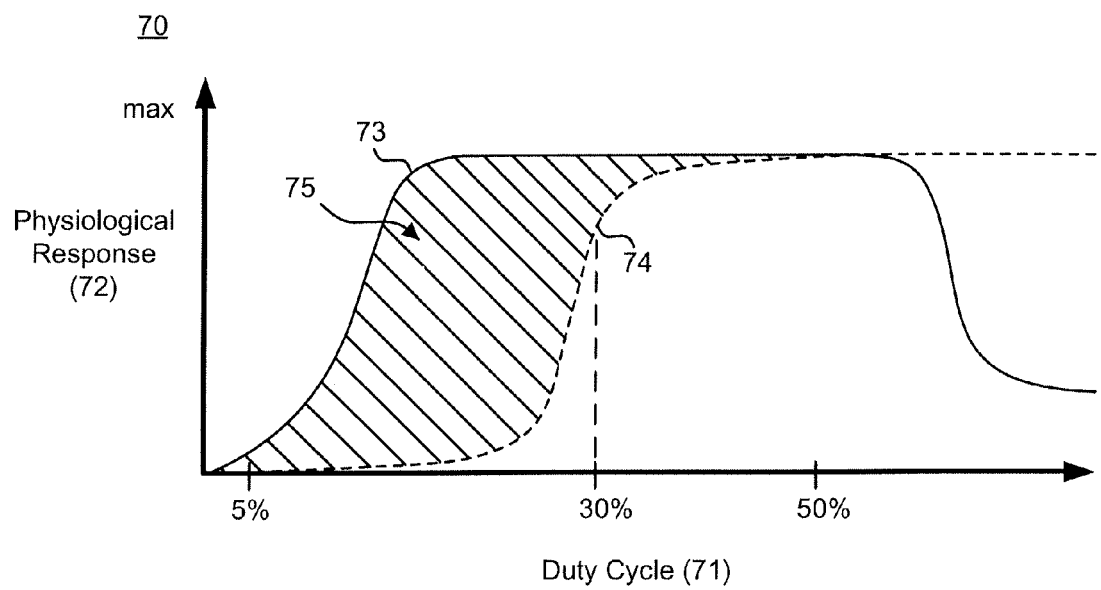
FIG. 5 is a graph showing, by way of example, the relationship between the targeted therapeutic efficacy and the extent of potential side effects resulting from use of the implantable neurostimulator of FIG. 1.

A "duty cycle" is the percentage of time that the neurostimulator 12 is stimulating, that is, the percentage of ON times. The VNS can be delivered with a periodic duty cycle in the range of around 5% to 30%. The selection of duty cycle is a tradeoff between competing medical considerations. FIG. 5 is a graph 70 showing, by way of example, the relationship between the targeted therapeutic efficacy 73 and the extent of potential side effects 74 resulting from use of the implantable neurostimulator 12 of FIG. 1. The x-axis represents the duty cycle 71. The duty cycle is determined by dividing the stimulation time by the sum of the ON and OFF times of the neurostimulator 12. However, the stimulation time may also need to include ramp-up time and ramp-down time, where the stimulation frequency exceeds a minimum threshold (as further described below with reference to FIG. 7). The y-axis represents physiological response 72 to VNS therapy. The physiological response 72 can be expressed quantitatively for a given duty cycle 71 as a function of the targeted therapeutic efficacy 73 and the extent of potential side effects 74, as described infra. The maximum level of physiological response 72 ("max") signifies the highest point of targeted therapeutic efficacy 73 or potential side effects 74.

Targeted therapeutic efficacy 73 and the extent of potential side effects 74 can be expressed as functions of duty cycle 71 and physiological response 72. The targeted therapeutic efficacy 73 represents the intended effectiveness of VNS in provoking a beneficial physiological response for a given duty cycle and can be quantified by assigning values to the various acute and chronic factors that contribute to the physiological response 72 of the patient 10 due to the delivery of therapeutic VNS. Acute factors that contribute to the targeted therapeutic efficacy 73 include increase in heart rate variability and coronary flow, reduction in cardiac workload through vasodilation, and improvement in left ventricular relaxation. Chronic factors that contribute to the targeted therapeutic efficacy 73 include decreased parasympathetic activation and increased sympathetic activation, as well as decreased negative cytokine production, increased baroreflex sensitivity, increased respiratory gas exchange efficiency, favorable gene expression, renin-angiotensin-aldosterone system down-regulation, anti-arrhythmic, anti-apoptotic, and ectopy-reducing anti-inflammatory effects. These contributing factors can be combined in any manner to express the relative level of targeted therapeutic efficacy 73, including weighting particular effects more heavily than others or applying statistical or numeric functions based directly on or derived from observed physiological changes. Empirically, targeted therapeutic efficacy 73 steeply increases beginning at around a 5% duty cycle, and levels off in a plateau near the maximum level of physiological response at around a 30% duty cycle. Thereafter, targeted therapeutic efficacy 73 begins decreasing at around a 50% duty cycle and continues in a plateau near a 25% physiological response through the maximum 100% duty cycle.

The extent of potential side effects 74 represents the occurrence of a possible physiological effect, either adverse or therapeutic, that is secondary to the benefit intended, which presents in the patient 10 in response to VNS and can be quantified by assigning values to the physiological effects presented due to the delivery of therapeutic VNS. The degree to which a patient 10 may be prone to exhibit side effects depends in large part upon the patient's condition, including degree of cardiac dysfunction, both acute and chronic, any comobidities, prior heart problems, family history, general health, and similar considerations. As well, the type and severity of a side effect is patient-dependent. For VNS in general, the more common surgical- and stimulation-related adverse side effects include infection, asystole, bradycardia, syncope, abnormal thinking, aspiration pneumonia, device site reaction, acute renal failure, nerve paralysis, hypesthesia, facial paresis, vocal cord paralysis, facial paralysis, hemidiaphragm paralysis, recurrent laryngeal injury, urinary retention, and low grade fever. The more common non-adverse side effects include hoarseness (voice alteration), increased coughing, pharyngitis, paresthesia, dyspnea, dyspepsia, nausea, and laryngismus. Less common side effects, including adverse events, include ataxia, hypesthesia, increase coughing, insomnia, muscle movement or twitching associated with stimulation, nausea, pain, paresthesia, pharyngitis, vomiting, aspiration, blood clotting, choking sensation, nerve damage, vasculature damage, device migration or extrusion, dizziness, dysphagia, duodenal or gastric ulcer, ear pain, face flushing, facial paralysis or paresis, implant rejection, fibrous tissue formation, fluid pocket formation, hiccupping, incision site pain, irritability, laryngeal irritation, hemidiaphragm paralysis, vocal cord paralysis, muscle pain, neck pain, painful or irregular stimulation, seroma, skin or tissue reaction, stomach discomfort, tinnitus, tooth pain, unusual scarring at incision site, vagus nerve paralysis, weight change, worsening of asthma or bronchitis. These quantified physiological effects can be combined in any manner to express the relative level of extent of potential side effects 74, including weighting particular effects more heavily than others or applying statistical or numeric functions based directly on or derived from observed physiological changes. Empirically, the extent of potential side effects 74 is initially low until around a 25% duty cycle, at which point the potential begins to steeply increase. The extent of potential side effects 74 levels off in a plateau near the maximum level of physiological response at around a 50% duty cycle through the maximum 100% duty cycle.

Figure 6:
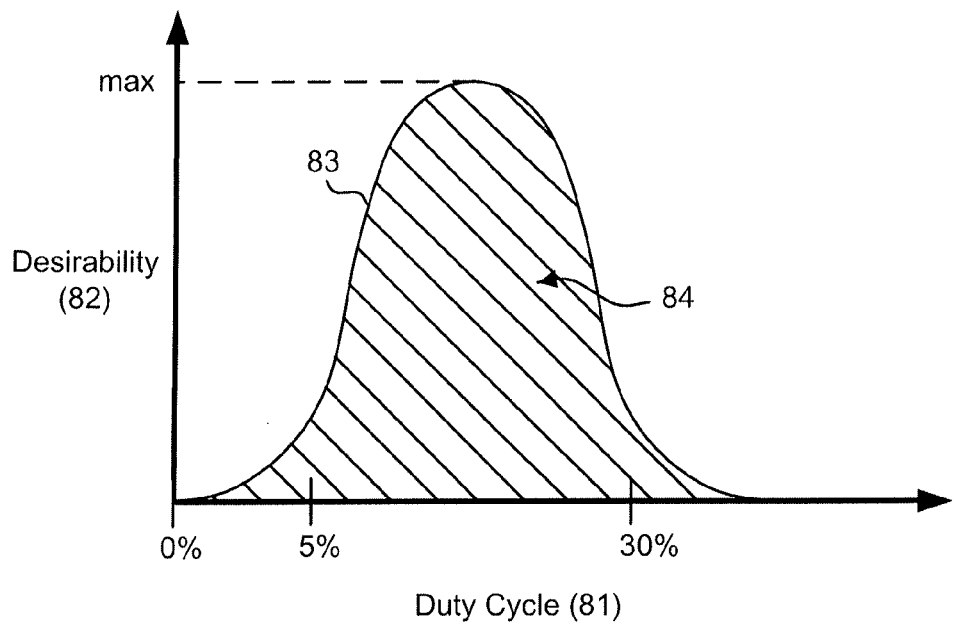
FIG. 6 is a graph showing, by way of example, the optimal duty cycle range based on the intersection depicted in FIG. 5.

The intersection 75 of the targeted therapeutic efficacy 73 and the extent of potential side effects 74 represents the optimal duty cycle range for VNS. FIG. 6 is a graph 80 showing, by way of example, the optimal duty cycle range 83 based on the intersection 75 depicted in FIG. 5. The x-axis represents the duty cycle 81 as a percentage of stimulation time over inhibition time. The y-axis represents the desirability 82 of operating the neurostimulator 12 at a given duty cycle 81. The optimal duty range 83 is a function 84 of the intersection 74 of the targeted therapeutic efficacy 73 and the extent of potential side effects 74. The desirability 82 can be expressed quantitatively for a given duty cycle 81 as a function of the values of the targeted therapeutic efficacy 73 and the extent of potential side effects 74 at their point of intersection in the graph 70 of FIG. 5. The maximum level of desirability 82 ("max") signifies a tradeoff that occurs at the point of highest targeted therapeutic efficacy 73 in light of lowest potential side effects 74 and that point will typically be found within the range of a 5% to 30% duty cycle 81. Other expressions of duty cycles and related factors are possible.

The neurostimulator 12 delivers VNS according to stored stimulation parameters, which are programmed using an external programmer 40 (shown in FIG. 3). Each stimulation parameter can be independently programmed to define the characteristics of the cycles of therapeutic stimulation and inhibition to ensure optimal stimulation for a patient 10. The programmable stimulation parameters affecting stimulation include output current, signal frequency, pulse width, signal ON time, signal OFF time, magnet activation (for VNS specifically triggered by "magnet mode"), "AutoStim" activation (delivered upon detection of a biological signal indicative of physiological conditions, such as bradycardia or asystole), and reset parameters. Other programmable parameters are possible.

Figure 7:
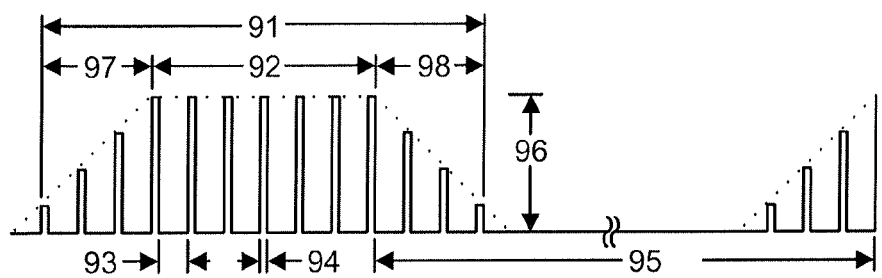
FIG. 7 is a timing diagram showing, by way of example, a stimulation cycle and an inhibition cycle of VNS as provided by implantable neurostimulator of FIG. 1.

VNS is delivered in alternating cycles of stimuli application and stimuli inhibition that are tuned to both efferently activate the heart's intrinsic nervous system and heart tissue and afferently activate the patient's central reflexes. FIG. 7 is a timing diagram showing, by way of example, a stimulation cycle and an inhibition cycle of VNS 90 as provided by implantable neurostimulator 12 of FIG. 1. The stimulation parameters enable the electrical stimulation pulse output by the neurostimulator 12 to be varied by both amplitude (output current 96) and duration (pulse width 94). The number of output pulses delivered per second determines the signal frequency 93. In one embodiment, a pulse width in the range of 100 to 250 μsee delivers between 0.02 and 50 mA of output current at a signal frequency of about 20 Hz, although other therapeutic values could be used as appropriate In the simplest case, the stimulation time is the time period during which the neurostimulator 12 is ON and delivering pulses of stimulation. The OFF time 95 is always the time period occurring in-between stimulation times 91 during which the neurostimulator 12 is OFF and inhibited from delivering stimulation. In one embodiment, the neurostimulator 12 implements a ramp-up time 97 and a ramp-down time 98 that respectively precede and follow the ON time 92 during which the neurostimulator 12 is ON and delivering pulses of stimulation at the full output current 96. The ramp-up time 97 and ramp-down time 98 are used when the stimulation frequency is at least 10 Hz, although other minimum thresholds could be used, and both times last two seconds, although other time periods could also be used. The ramp-up time 97 and ramp-down time 98 allow the strength of the output current 96 of each output pulse to be gradually increased and decreased, thereby avoiding unnecessary trauma to the vagus nerve due to sudden delivery or inhibition of stimulation at full strength.

While the invention has been particularly shown and described as referenced to the embodiments thereof, those skilled in the art will understand that the foregoing and other changes in form and detail may be made therein without departing from the spirit and scope.

What is claimed is:

1. A vagus nerve neurostimulator for modulating autonomic cardiovascular drive, comprising:
   a pulse generator, wherein the pulse generator generates a pulsed electrical signal comprising:
      a signal ON time;
      a signal OFF time;
      an output current;
      a signal frequency of approximately 10 Hz;
      a pulse width; and
      a duty cycle defined by dividing the signal ON time by the sum of the signal ON time and signal OFF time;
   a therapy lead;
   an electrode communicatively coupled to the pulse generator via the therapy lead, wherein the electrical signal is applied to a vagus nerve via the electrode to propagate action potentials in both afferent and efferent directions along the vagus nerve at an intensity that avoids acute physiological side effects; and
   a leadless heart rate sensor.

2. The vagus nerve neurostimulator according to claim 1, wherein the pulsed electrical signal further comprises a signal ramp-up time.

3. The vagus nerve neurostimulator according to claim 1, wherein the pulsed electrical signal further comprises a signal ramp-down time.

4. The vagus nerve neurostimulator according to claim 1, wherein the duty cycle comprises a value in a range of 5% to 20%.

5. The vagus nerve neurostimulator according to claim 1, wherein application of the electrical signal to the vagus nerve further induces heart rate variability during the signal ON time.

6. The vagus nerve neurostimulator according to claim 1, wherein the pulsed electrical signal further comprises a ramp-up time and a ramp-down time; and
   application of the electrical signal to the vagus nerve further induces heart rate variability during the ramp-up time, the signal ON time, and the ramp-down time.

7. The vagus nerve neurostimulator according to claim 1, wherein the leadless heart rate sensor is configured to continually monitor heart rate against a stored baseline heart rate.

8. The vagus nerve neurostimulator according to claim 7, wherein the vagus nerve neurostimulator is further configured to suspend application of the electrical signal to the vagus nerve for a fixed period of time in response to the monitored heart falling below a stored lower bound.

9. The vagus nerve neurostimulator according to claim 7, wherein the vagus nerve neurostimulator is further configured to gradually down titrate the electrical signal in response to the monitored heart rate falling below a stored lower bound.

10. The vagus nerve neurostimulator according to claim 7, wherein the vagus nerve neurostimulator is further configured to gradually up titrate the electrical signal in response to the monitored heart rate rising above a stored upper bound.

11. A vagus nerve neurostimulator for modulating autonomic cardiovascular drive, comprising:
a pulse generator, wherein the pulse generator generates a pulsed electrical signal comprising:
a signal ramp-up time;
a signal ramp-down time;
a signal ON time;
a signal OFF time;
an output current;
a signal frequency of approximately 10 Hz;
a pulse width; and
a duty cycle defined by dividing the signal ON time by the sum of the signal ON time and signal OFF time;
a therapy lead;
an electrode communicatively coupled to the pulse generator via the therapy lead, wherein the electrical signal is applied to a vagus nerve via the electrode to propagate action potentials in both afferent and efferent directions along the vagus nerve at an intensity that avoids acute physiological side effects; and
a leadless heart rate sensor.

12. The vagus nerve neurostimulator according to claim 11, wherein application of the electrical signal to the vagus nerve further induces heart rate variability during the ramp-up time, the signal ON time, and the ramp-down time.

13. The vagus nerve neurostimulator according to claim 11, wherein the signal ramp-up time is two seconds.

14. The vagus nerve neurostimulator according to claim 11, wherein the signal ramp-down time is two seconds.

15. The vagus nerve neurostimulator according to claim 11, wherein the output current, the signal frequency or the pulse width of the pulsed electrical signal is modified during the ramp-up time.

16. The vagus nerve neurostimulator according to claim 11, wherein the output current, the signal frequency or the pulse width of the pulsed electrical signal is modified during the ramp-down time.

17. A vagus nerve neurostimulator for modulating autonomic cardiovascular drive, comprising:
a pulse generator, wherein the pulse generator generates a pulsed electrical signal comprising:
a signal ON time;
a signal OFF time;
an output current;
a signal frequency of approximately 10 Hz;
a pulse width; and
a duty cycle defined by dividing the signal ON time by the sum of the signal ON time and signal OFF time;
a therapy lead;
an electrode communicatively coupled to the pulse generator via the therapy lead, wherein the electrical signal is applied to a vagus nerve via the electrode to:
propagate action potentials in both afferent and efferent directions along the vagus nerve; and
induce heart rate variability during the signal ON time at an intensity that avoids acute physiological side effects; and
a leadless heart rate sensor.

18. The vagus nerve neurostimulator according to claim 17, wherein the pulsed electrical signal further comprises a signal ramp-up time.

19. The vagus nerve neurostimulator according to claim 17, wherein the pulsed electrical signal further comprises a signal ramp-down time.

20. The vagus nerve neurostimulator according to claim 17, wherein the duty cycle comprises a value in a range of 5% to 20%.

* * * * *